US012686891B2

(12) United States Patent
Anderson et al.

(10) Patent No.: US 12,686,891 B2
(45) Date of Patent: Jul. 21, 2026

(54) SILICA-BASED CHROMATOGRAPHIC PROCESSES FOR ISOLATING NUCLEIC ACID-PROTEIN COMPLEXES AND DETECTING TARGET NUCLEIC ACIDS

(71) Applicant: ARIZONA BOARD OF REGENTS ON BEHALF OF ARIZONA STATE UNIVERSITY, Scottsdale, AZ (US)

(72) Inventors: Karen Anderson, Scottsdale, AZ (US); Mark Knappenberger, Mesa, AZ (US); Siril Arockiam, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 545 days.

(21) Appl. No.: 18/255,731

(22) PCT Filed: Dec. 2, 2021

(86) PCT No.: PCT/US2021/061578
§ 371 (c)(1),
(2) Date: Jun. 2, 2023

(87) PCT Pub. No.: WO2022/120027
PCT Pub. Date: Jun. 9, 2022

(65) Prior Publication Data
US 2024/0102113 A1 Mar. 28, 2024

Related U.S. Application Data

(60) Provisional application No. 63/255,358, filed on Oct. 13, 2021, provisional application No. 63/120,680, filed on Dec. 2, 2020.

(51) Int. Cl.
*C12Q 1/70* (2006.01)
*C12N 9/22* (2006.01)
(Continued)

(52) U.S. Cl.
CPC .................. *C12Q 1/70* (2013.01); *C12N 9/22* (2013.01); *C12N 15/11* (2013.01); *C12Q 1/6818* (2013.01);
(Continued)

(58) Field of Classification Search
CPC .......................... C12Q 1/6806; C12N 2310/20
See application file for complete search history.

(56) References Cited

U.S. PATENT DOCUMENTS

2008/0139801 A1 6/2008 Unmasky et al.
2014/0356867 A1* 12/2014 Peter ........................ C12N 9/22
536/23.1
(Continued)

FOREIGN PATENT DOCUMENTS

WO 2007121717 A1 11/2007
WO WO-2016028843 A2 * 2/2016 ............... C12N 9/22
WO WO-2021211950 A1 * 10/2021 ........... C12Q 1/6816

OTHER PUBLICATIONS

O'Connell et al.; Programmable RNA recognition and cleavage by CRISPR/Cas9. Nature. Dec. 11, 2014;516(7530):263-6. doi: 10.1038/nature13769. Epub Sep. 28, 2014. PMID: 25274302; PMCID: PMC4268322 (Year: 2014).*
(Continued)

*Primary Examiner* — Aaron A Priest
*Assistant Examiner* — Tian Yu
(74) *Attorney, Agent, or Firm* — Quarles & Brady LLP

(57) ABSTRACT

The disclosure relates to methods of detecting a target nucleic acid in a sample using a deactivated RNA-guided nuclease and guide RNA complex. Some methods relate to isolating protein-nucleic acid complexes using silica-based chromatography with certain buffered solutions to better prevent complex dissociation. Some methods relate to isolating protein-nucleic acid complexes using a tagged ribo-
(Continued)

nucleoprotein which binds to a target nucleic acid to form a detectable interconnected network comprising the target nucleic acid. Also provided herein are primer nucleic acids, buffer solutions, and kits for performing the methods of this disclosure for detecting a target nucleic acid in a sample.

17 Claims, 6 Drawing Sheets

Specification includes a Sequence Listing.

(51) Int. Cl.
*C12N 15/11* (2006.01)
*C12Q 1/6806* (2018.01)
*C12Q 1/6818* (2018.01)
*C12Q 1/6844* (2018.01)

(52) U.S. Cl.
CPC ........ *C12N 2310/20* (2017.05); *C12Q 1/6806* (2013.01); *C12Q 1/6844* (2013.01)

(56) References Cited

U.S. PATENT DOCUMENTS

| | | |
|---|---|---|
| 2019/0382758 A1 | 12/2019 | Aoki et al. |
| 2021/0325379 A1 | 10/2021 | Lindsay et al. |

OTHER PUBLICATIONS

Slesarev et al. ; CRISPR/CAS9 targeted Capture of mammalian genomic regions for characterization by NGS. Sci Rep. Mar. 5, 2019;9(1):3587. doi: 10.1038/s41598-019-39667-4. PMID: 30837529; PMCID: PMC6401131 (Year: 2019).*

MilliporeSigma (Product information: dCas9-3xFLAG-Biotin Protein (2019)) (Year: 2019).*

Oakes et al.; Profiling of engineering hotspots identifies an allosteric CRISPR-Cas9 switch. Nat Biotechnol. Jun. 2016;34(6):646-51. doi: 10.1038/nbt.3528. Epub May 2, 2016. PMID: 27136077; PMCID: PMC4900928 (Year: 2016).*

International Search Report and Written Opinion for corresponding International Application PCT/US2021/061578, mailed May 5, 2022.

Mautner et al., "Rapid point of care detection of Sars COV2 using reverse transcription loop mediated isothermal amplification (RT LAMP)." pp. 1-14, Virology Journal, vol. 17, No. 1, Oct. 21, 2020; abstract; doi:10.1186/s12985-020-01435-6.

Sigma-Aldrich. "Product Specification, Product No. W0263." Product data sheet and website (online). Retrieved from the internet; https://sigmaaldrich.com/specification-sheets/792/783/W0263-375ML-KC_SIGMA_pdf. Oct. 6, 2010; pp. 1-3.

Tijssen, P., editor. 1993. Laboratory Techniques in Biochemistry and Molecular Biology: Hybridization with Nucleic Acid Probes, part I, chapter 2, "Overview of principles of hybridization and the strategy of nucleic acid probe assays" (vol. 24, Part II, Elsevier B.V., N.Y.).

Tsumoto et al., "Arginine improves protein elution in hydrophobic interaction chromatography, The cases of human interleukin-6 an activin-A." pp. 81-86, Journal of Chromatography, vol. 1154, Nos. 1-2, Jun. 22, 2007; abstract; doi: 10.1016/j.chroma.2007.02.061.

Wu et al., "A new coronavirus associated with huma respiratory disease in China." pp. 265-269, Nature, vol. 579, No. 7998, Feb. 3, 2020; abstract; Genbank Supplement, pp. 1, 10-11; doi: 10.1038/s41586-020-2008-3.

* cited by examiner apo-dCas9  dCas9:sgRNA  dCas9:sgRNA:Target pH 4 pH ~ 8.5

SEQUENCE LISTING

```
<160> NUMBER OF SEQ ID NOS: 67

<210> SEQ ID NO 1
<211> LENGTH: 20
<212> TYPE: DNA
<213> ORGANISM: Artificial Sequence
<220> FEATURE:
<223> OTHER INFORMATION: Synthetic- Spike_002-F3

<400> SEQUENCE: 1
acaatttggc agagacattg                                              20

<210> SEQ ID NO 2
<211> LENGTH: 22
<212> TYPE: DNA
<213> ORGANISM: Artificial Sequence
<220> FEATURE:
<223> OTHER INFORMATION: Synthetic- Spike_002_B3

<400> SEQUENCE: 2
caagtaggag taagttgatc tg                                            22

<210> SEQ ID NO 3
<211> LENGTH: 43
<212> TYPE: DNA
<213> ORGANISM: Artificial Sequence
<220> FEATURE:
<223> OTHER INFORMATION: Synthetic- Spike_002_FIP

<400> SEQUENCE: 3
gacaccacca aaagaacatg gtgctgacac tactgatgct gtc                     43

<210> SEQ ID NO 4
```

-continued

```
<211> LENGTH: 44
<212> TYPE: DNA
<213> ORGANISM: Artificial Sequence
<220> FEATURE:
<223> OTHER INFORMATION: Synthetic- Spike_002_BIP

<400> SEQUENCE: 4
ccaggaacaa atacttctaa ccaggtgaat agcaacaggg actt                    44

<210> SEQ ID NO 5
<211> LENGTH: 24
<212> TYPE: DNA
<213> ORGANISM: Artificial Sequence
<220> FEATURE:
<223> OTHER INFORMATION: Synthetic- Spike_002_LF

<400> SEQUENCE: 5
tgtcaagaat ctcaagtgtc tgtg                                          24

<210> SEQ ID NO 6
<211> LENGTH: 25
<212> TYPE: DNA
<213> ORGANISM: Artificial Sequence
<220> FEATURE:
<223> OTHER INFORMATION: Synthetic- Spike_002_LB

<400> SEQUENCE: 6
ctttatcagg atgttaactg cacag                                         25

<210> SEQ ID NO 7
<211> LENGTH: 20
<212> TYPE: DNA
<213> ORGANISM: Artificial Sequence
<220> FEATURE:
<223> OTHER INFORMATION: Synthetic- ORF1ab_001_F3

<400> SEQUENCE: 7
ggctaactaa catctttggc                                               20

<210> SEQ ID NO 8
<211> LENGTH: 18
<212> TYPE: DNA
<213> ORGANISM: Artificial Sequence
<220> FEATURE:
<223> OTHER INFORMATION: Synthetic- ORF1ab_001_B3

<400> SEQUENCE: 8
gtcagcacac aaagccaa                                                 18

<210> SEQ ID NO 9
<211> LENGTH: 48
<212> TYPE: DNA
<213> ORGANISM: Artificial Sequence
<220> FEATURE:
<223> OTHER INFORMATION: Synthetic- ORF1ab_001_FIP

<400> SEQUENCE: 9
gtctctaaga aactctacac cttcctgttt atgaaaaact caaacccg                48

<210> SEQ ID NO 10
<211> LENGTH: 44
<212> TYPE: DNA
<213> ORGANISM: Artificial Sequence
<220> FEATURE:
<223> OTHER INFORMATION: Synthetic- ORF1ab_001_BIP

<400> SEQUENCE: 10
```
tatctcaacc tgtgcttgtg aaaagaatgt ctgaacactc tcct                    44

<210> SEQ ID NO 11
<211> LENGTH: 24
<212> TYPE: DNA
<213> ORGANISM: Artificial Sequence
<220> FEATURE:
<223> OTHER INFORMATION: Synthetic- ORF1ab_001_LB

<400> SEQUENCE: 11
acaaattgtc acctgtgcaa agga                                          24

<210> SEQ ID NO 12
<211> LENGTH: 18
<212> TYPE: DNA
<213> ORGANISM: Artificial Sequence
<220> FEATURE:
<223> OTHER INFORMATION: Synthetic- N2_001-F3

<400> SEQUENCE: 12
ccccgcatta cgtttggt                                                 18

<210> SEQ ID NO 13
<211> LENGTH: 20
<212> TYPE: DNA
<213> ORGANISM: Artificial Sequence
<220> FEATURE:
<223> OTHER INFORMATION: Synthetic- N2_001-B3

<400> SEQUENCE: 13
agccaatttg gtcatctgga                                               20

<210> SEQ ID NO 14
<211> LENGTH: 41
<212> TYPE: DNA
<213> ORGANISM: Artificial Sequence
<220> FEATURE:
<223> OTHER INFORMATION: Synthetic- N2_001-FIP

<400> SEQUENCE: 14
gttgttttga tcgcgcccca cggaccctca gattcaactg g                       41

<210> SEQ ID NO 15
<211> LENGTH: 41
<212> TYPE: DNA
<213> ORGANISM: Artificial Sequence
<220> FEATURE:
<223> OTHER INFORMATION: Synthetic- N2_001-BIP

<400> SEQUENCE: 15
cgtcttggtt caccgctctc atggtgttaa ttggaacgcc t                       41

<210> SEQ ID NO 16
<211> LENGTH: 22
<212> TYPE: DNA
<213> ORGANISM: Artificial Sequence
<220> FEATURE:
<223> OTHER INFORMATION: Synthetic- N2_001-LF

<400> SEQUENCE: 16
gcgttctcca ttctggttac tg                                            22

<210> SEQ ID NO 17
<211> LENGTH: 21
<212> TYPE: DNA

-continued

<213> ORGANISM: Artificial Sequence
<220> FEATURE:
<223> OTHER INFORMATION: Synthetic- N2_001-LB

<400> SEQUENCE: 17
ctcaacatgg caaggaagac c                                                        21

<210> SEQ ID NO 18
<211> LENGTH: 19
<212> TYPE: DNA
<213> ORGANISM: Artificial Sequence
<220> FEATURE:
<223> OTHER INFORMATION: Synthetic- 18S_rRNA-F3

<400> SEQUENCE: 18
tggtggagcg atttgtctg                                                          19

<210> SEQ ID NO 19
<211> LENGTH: 19
<212> TYPE: DNA
<213> ORGANISM: Artificial Sequence
<220> FEATURE:
<223> OTHER INFORMATION: Synthetic- 18S_rRNA-B3

<400> SEQUENCE: 19
tgagccagtc agtgtagcg                                                          19

<210> SEQ ID NO 20
<211> LENGTH: 40
<212> TYPE: DNA
<213> ORGANISM: Artificial Sequence
<220> FEATURE:
<223> OTHER INFORMATION: Synthetic- 18S_rRNA-FIP

<400> SEQUENCE: 20
aagaagttgg gggacgccga acgagactct ggcatgctaa                                   40

<210> SEQ ID NO 21
<211> LENGTH: 38
<212> TYPE: DNA
<213> ORGANISM: Artificial Sequence
<220> FEATURE:
<223> OTHER INFORMATION: Synthetic- 18S_rRNA-BIP

<400> SEQUENCE: 21
ggacaagtgg cgttcagcca agccccggac atctaagg                                     38

<210> SEQ ID NO 22
<211> LENGTH: 22
<212> TYPE: DNA
<213> ORGANISM: Artificial Sequence
<220> FEATURE:
<223> OTHER INFORMATION: Synthetic- 18S_rRNA-LB

<400> SEQUENCE: 22
cccgagattg agcaataaca gg                                                      22

<210> SEQ ID NO 23
<211> LENGTH: 20
<212> TYPE: DNA
<213> ORGANISM: Artificial Sequence
<220> FEATURE:
<223> OTHER INFORMATION: Synthetic- ACTB_001-F3

<400> SEQUENCE: 23
ggcatccacg aaactacctt                                                         20

-continued

```
<210> SEQ ID NO 24
<211> LENGTH: 19
<212> TYPE: DNA
<213> ORGANISM: Artificial Sequence
<220> FEATURE:
<223> OTHER INFORMATION: Synthetic- ACTB_001-B3

<400> SEQUENCE: 24
gccgatccac acggagtac                                                    19

<210> SEQ ID NO 25
<211> LENGTH: 40
<212> TYPE: DNA
<213> ORGANISM: Artificial Sequence
<220> FEATURE:
<223> OTHER INFORMATION: Synthetic- ACTB_001-FIP

<400> SEQUENCE: 25
tgccgccaga cagcactgtg tgaagtgtga cgtggacatc                             40

<210> SEQ ID NO 26
<211> LENGTH: 39
<212> TYPE: DNA
<213> ORGANISM: Artificial Sequence
<220> FEATURE:
<223> OTHER INFORMATION: Synthetic- ACTB_001-BIP

<400> SEQUENCE: 26
ttgccgacag gatgcagaag ggcgctcagg aggagcaat                              39

<210> SEQ ID NO 27
<211> LENGTH: 18
<212> TYPE: DNA
<213> ORGANISM: Artificial Sequence
<220> FEATURE:
<223> OTHER INFORMATION: Synthetic- ACTB_001-LF

<400> SEQUENCE: 27
ggcgtacagg tctttgcg                                                     18

<210> SEQ ID NO 28
<211> LENGTH: 20
<212> TYPE: DNA
<213> ORGANISM: Artificial Sequence
<220> FEATURE:
<223> OTHER INFORMATION: Synthetic- ACTB_001-LB

<400> SEQUENCE: 28
ccctggcacc cagcacaatg                                                   20

<210> SEQ ID NO 29
<211> LENGTH: 17
<212> TYPE: DNA
<213> ORGANISM: Artificial Sequence
<220> FEATURE:
<223> OTHER INFORMATION: Synthetic- ACTB_002-F3

<400> SEQUENCE: 29
gcgcggctac agcttca                                                      17

<210> SEQ ID NO 30
<211> LENGTH: 18
<212> TYPE: DNA
<213> ORGANISM: Artificial Sequence
<220> FEATURE:
```

-continued

<223> OTHER INFORMATION: Synthetic- ACTB_002-B3

<400> SEQUENCE: 30
ggaagagtgc ctcagggc                                              18

<210> SEQ ID NO 31
<211> LENGTH: 37
<212> TYPE: DNA
<213> ORGANISM: Artificial Sequence
<220> FEATURE:
<223> OTHER INFORMATION: Synthetic- ACTB_002-FIP

<400> SEQUENCE: 31
aagtccaggg cgacgtagca ccggccgagc gggaaat                         37

<210> SEQ ID NO 32
<211> LENGTH: 41
<212> TYPE: DNA
<213> ORGANISM: Artificial Sequence
<220> FEATURE:
<223> OTHER INFORMATION: Synthetic- ACTB_002-BIP

<400> SEQUENCE: 32
gagatggcca cggctgcttc cattgccaat ggtgatgacc t                    41

<210> SEQ ID NO 33
<211> LENGTH: 21
<212> TYPE: DNA
<213> ORGANISM: Artificial Sequence
<220> FEATURE:
<223> OTHER INFORMATION: Synthetic- ACTB_002-LF

<400> SEQUENCE: 33
ttctccttaa tgtcacgcac g                                          21

<210> SEQ ID NO 34
<211> LENGTH: 21
<212> TYPE: DNA
<213> ORGANISM: Artificial Sequence
<220> FEATURE:
<223> OTHER INFORMATION: Synthetic- ACTB_002-LB

<400> SEQUENCE: 34
ccctggagaa gagctacgag c                                          21

<210> SEQ ID NO 35
<211> LENGTH: 19
<212> TYPE: DNA
<213> ORGANISM: Artificial Sequence
<220> FEATURE:
<223> OTHER INFORMATION: Synthetic- ACTB_003-F3

<400> SEQUENCE: 35
ccctgaagta ccccatcga                                             19

<210> SEQ ID NO 36
<211> LENGTH: 20
<212> TYPE: DNA
<213> ORGANISM: Artificial Sequence
<220> FEATURE:
<223> OTHER INFORMATION: Synthetic- ACTB_003-B3

<400> SEQUENCE: 36
tggggtgttg aaggtctcaa                                            20

```
<210> SEQ ID NO 37
<211> LENGTH: 40
<212> TYPE: DNA
<213> ORGANISM: Artificial Sequence
<220> FEATURE:
<223> OTHER INFORMATION: Synthetic- ACTB_003-FIP

<400> SEQUENCE: 37
agccacacgc agctcattgt agcacggcat cgtcaccaac                                    40

<210> SEQ ID NO 38
<211> LENGTH: 37
<212> TYPE: DNA
<213> ORGANISM: Artificial Sequence
<220> FEATURE:
<223> OTHER INFORMATION: Synthetic- ACTB_003-BIP

<400> SEQUENCE: 38
agcaccccgt gctgctgagt catcttctcg cggttgg                                       37

<210> SEQ ID NO 39
<211> LENGTH: 22
<212> TYPE: DNA
<213> ORGANISM: Artificial Sequence
<220> FEATURE:
<223> OTHER INFORMATION: Synthetic- ACTB_003-LF

<400> SEQUENCE: 39
ccagattttc tccatgtcgt cc                                                       22

<210> SEQ ID NO 40
<211> LENGTH: 16
<212> TYPE: DNA
<213> ORGANISM: Artificial Sequence
<220> FEATURE:
<223> OTHER INFORMATION: Synthetic- ACTB_004-F3

<400> SEQUENCE: 40
tgctgctgac cgaggc                                                              16

<210> SEQ ID NO 41
<211> LENGTH: 17
<212> TYPE: DNA
<213> ORGANISM: Artificial Sequence
<220> FEATURE:
<223> OTHER INFORMATION: Synthetic- ACTB_004-B3

<400> SEQUENCE: 41
gcacagtgtg ggtgacc                                                             17

<210> SEQ ID NO 42
<211> LENGTH: 41
<212> TYPE: DNA
<213> ORGANISM: Artificial Sequence
<220> FEATURE:
<223> OTHER INFORMATION: Synthetic- ACTB_004-FIP

<400> SEQUENCE: 42
atggctgggg tgttgaaggt ctctgaaccc caaggccaac c                                  41

<210> SEQ ID NO 43
<211> LENGTH: 40
<212> TYPE: DNA
<213> ORGANISM: Artificial Sequence
<220> FEATURE:
<223> OTHER INFORMATION: Synthetic- ACTB_004-BIP
```

-continued

<400> SEQUENCE: 43
tacgttgcta tccaggctgt gccaccggag tccatcacga                                40

<210> SEQ ID NO 44
<211> LENGTH: 18
<212> TYPE: DNA
<213> ORGANISM: Artificial Sequence
<220> FEATURE:
<223> OTHER INFORMATION: Synthetic- N.F3

<400> SEQUENCE: 44
tggaccccaa aatcagcg                                                        18

<210> SEQ ID NO 45
<211> LENGTH: 20
<212> TYPE: DNA
<213> ORGANISM: Artificial Sequence
<220> FEATURE:
<223> OTHER INFORMATION: Synthetic- N.B3

<400> SEQUENCE: 45
agccaatttg gtcatctgga                                                      20

<210> SEQ ID NO 46
<211> LENGTH: 41
<212> TYPE: DNA
<213> ORGANISM: Artificial Sequence
<220> FEATURE:
<223> OTHER INFORMATION: Synthetic- N.FIP

<400> SEQUENCE: 46
gttgttttga tcgcgcccca cattacgttt ggtggaccct c                             41

<210> SEQ ID NO 47
<211> LENGTH: 41
<212> TYPE: DNA
<213> ORGANISM: Artificial Sequence
<220> FEATURE:
<223> OTHER INFORMATION: Synthetic- N.BIP

<400> SEQUENCE: 47
atactgcgtc ttggttcacc gcattggaac gccttgtcct c                             41

<210> SEQ ID NO 48
<211> LENGTH: 22
<212> TYPE: DNA
<213> ORGANISM: Artificial Sequence
<220> FEATURE:
<223> OTHER INFORMATION: Synthetic- N.LF

<400> SEQUENCE: 48
ctggttactg ccagttgaat ct                                                   22

<210> SEQ ID NO 49
<211> LENGTH: 23
<212> TYPE: DNA
<213> ORGANISM: Artificial Sequence
<220> FEATURE:
<223> OTHER INFORMATION: Synthetic- N.LB

<400> SEQUENCE: 49
tctcactcaa catggcaagg aag                                                  23

<210> SEQ ID NO 50
<211> LENGTH: 19

-continued

```
<212> TYPE: DNA
<213> ORGANISM: Artificial Sequence
<220> FEATURE:
<223> OTHER INFORMATION: Synthetic- 18s_rRNA-F3

<400> SEQUENCE: 50
tggtggagcg atttgtctg                                                      19

<210> SEQ ID NO 51
<211> LENGTH: 19
<212> TYPE: DNA
<213> ORGANISM: Artificial Sequence
<220> FEATURE:
<223> OTHER INFORMATION: Synthetic- 18s_rRNA-B3

<400> SEQUENCE: 51
tgagccagtc agtgtagcg                                                      19

<210> SEQ ID NO 52
<211> LENGTH: 40
<212> TYPE: DNA
<213> ORGANISM: Artificial Sequence
<220> FEATURE:
<223> OTHER INFORMATION: Synthetic- 18s_rRNA-FIP

<400> SEQUENCE: 52
aagaagttgg gggacgccga acgagactct ggcatgctaa                               40

<210> SEQ ID NO 53
<211> LENGTH: 38
<212> TYPE: DNA
<213> ORGANISM: Artificial Sequence
<220> FEATURE:
<223> OTHER INFORMATION: Synthetic- 18s_rRNA-BIP

<400> SEQUENCE: 53
ggacaagtgg cgttcagcca agccccggac atctaagg                                 38

<210> SEQ ID NO 54
<211> LENGTH: 22
<212> TYPE: DNA
<213> ORGANISM: Artificial Sequence
<220> FEATURE:
<223> OTHER INFORMATION: Synthetic- 18s_rRNA-LoopB

<400> SEQUENCE: 54
cccgagattg agcaataaca gg                                                  22

<210> SEQ ID NO 55
<211> LENGTH: 20
<212> TYPE: RNA
<213> ORGANISM: Artificial Sequence
<220> FEATURE:
<223> OTHER INFORMATION: Synthetic- N gene SARS-CoV-2 target sequence

<400> SEQUENCE: 55
gggcgcgauc aaaacaacgu                                                     20

<210> SEQ ID NO 56
<211> LENGTH: 62
<212> TYPE: RNA
<213> ORGANISM: Artificial Sequence
<220> FEATURE:
<223> OTHER INFORMATION: Synthetic- SARS-CoV-2 N gene sgRNA

<400> SEQUENCE: 56
```

```
gggcgcgauc aaaacaacgu guuuuagagc uagaaauagc aaguuaaaau aaggcuaguc    60
cg                                                                   62

<210> SEQ ID NO 57
<211> LENGTH: 62
<212> TYPE: DNA
<213> ORGANISM: Artificial Sequence
<220> FEATURE:
<223> OTHER INFORMATION: Synthetic- SARS-CoV-2 Spike 1: 5'

<400> SEQUENCE: 57
tctaaagccg aaaaaccctg guuuuagagc uagaaauagc aaguuaaaau aaggcuaguc    60
cg                                                                   62

<210> SEQ ID NO 58
<211> LENGTH: 62
<212> TYPE: DNA
<213> ORGANISM: Artificial Sequence
<220> FEATURE:
<223> OTHER INFORMATION: Synthetic- SARS-CoV-2 Spike 2: 5'

<400> SEQUENCE: 58
gctacactac gtgcccgccg guuuuagagc uagaaauagc aaguuaaaau aaggcuaguc    60
cg                                                                   62

<210> SEQ ID NO 59
<211> LENGTH: 62
<212> TYPE: DNA
<213> ORGANISM: Artificial Sequence
<220> FEATURE:
<223> OTHER INFORMATION: Synthetic- SARS-CoV-2 RdRP 1: 5'

<400> SEQUENCE: 59
agttgtggca tctcctgatg guuuuagagc uagaaauagc aaguuaaaau aaggcuaguc    60
cg                                                                   62

<210> SEQ ID NO 60
<211> LENGTH: 62
<212> TYPE: DNA
<213> ORGANISM: Artificial Sequence
<220> FEATURE:
<223> OTHER INFORMATION: Synthetic- SARS-CoV-2 Matrix 1: 5'

<400> SEQUENCE: 60
ttgcgcgtac gcgttccatg guuuuagagc uagaaauagc aaguuaaaau aaggcuaguc    60
cg                                                                   62

<210> SEQ ID NO 61
<211> LENGTH: 62
<212> TYPE: DNA
<213> ORGANISM: Artificial Sequence
<220> FEATURE:
<223> OTHER INFORMATION: Synthetic- SARS-CoV-2 Matrix 2: 5'

<400> SEQUENCE: 61
caatacgaag atgtccacga guuuuagagc uagaaauagc aaguuaaaau aaggcuaguc    60
cg                                                                   62

<210> SEQ ID NO 62
<211> LENGTH: 20
<212> TYPE: DNA
<213> ORGANISM: Artificial Sequence
```

-continued

```
<220> FEATURE:
<223> OTHER INFORMATION: Synthetic- HPV16 E6

<400> SEQUENCE: 62
gcaacagtta ctgcgacgtg                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic- HPV18 E2_1

<400> SEQUENCE: 63
aaatgttata ggctggcacc                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic- HPV18 E2_2

<400> SEQUENCE: 64
acaagctgag tagcggatac                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic- HPV18 E6

<400> SEQUENCE: 65
ataaggtgcc tgcggtgcca                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic- HPV18 L1

<400> SEQUENCE: 66
tggcggccta gtgacaatac                                              20

<210> SEQ ID NO 67
<211> LENGTH: 16
<212> TYPE: PRT
<213> ORGANISM: Artificial Sequence
<220> FEATURE:
<223> OTHER INFORMATION: Synthetic- AviTag

<400> SEQUENCE: 67

Gly Leu Asn Asp Ile Phe Glu Ala Gln Lys Ile Glu Trp His Glu Ala
1               5                   10                  15
```

SILICA-BASED CHROMATOGRAPHIC PROCESSES FOR ISOLATING NUCLEIC ACID-PROTEIN COMPLEXES AND DETECTING TARGET NUCLEIC ACIDS

CROSS-REFERENCE TO RELATED APPLICATIONS

This application is the U.S. National Stage of PCT/US2021/061578, filed on Dec. 2, 2021, which claims priority to U.S. Provisional Application No. 63/255,358 filed on Oct. 13, 2021 and U.S. Provisional Application No. 63/120,680 filed on Dec. 2, 2020, the contents of which are incorporated by reference in their entireties.

SEQUENCE LISTING

This application is being filed electronically via EFS-Web and includes an electronically submitted Sequence Listing in .txt format. The .txt file contains a sequence listing entitled "112624_01312_ ST25.txt" created on Dec. 2, 2021 and is 14,128 bytes in size. The Sequence Listing contained in this .txt file is part of the specification and is hereby incorporated by reference herein in its entirety.

BACKGROUND

While silica-based chromatography has been widely utilized to isolate and purify nucleic acid species for decades, the binding conditions under which DNA adsorbs to silica substrates effectively are stringent and unamenable for retaining protein-DNA interactions, such as, e.g., DNA-CRISPR-RNP complexes. Conventional silica-based DNA isolation strategies incorporate very high amounts of chaotropic salts (e.g., guanidine-HCl) which, in solution, are believed to have the capability to shield oxidized surface silanols and form weak electrostatic connections to nucleic acids. High salt and low pH conditions permit adsorption of DNA to silica at high densities; however, these conditions also promote rapid denaturation of the vast majority of proteins. Thus, gentler conditions are desirable for silica-based DNA isolation methods where the conditions allow DNA adsorption and retain CRISPR-RNP complex stability. Accordingly, there remains a need in the art for improved methods for detecting target nucleic acids and isolating DNA-protein complexes using silica-based methods.

SUMMARY OF THE DISCLOSURE

In a first aspect, provided herein is a method for detecting a target nucleic acid in a sample using a ribonucleoprotein which specifically binds the target nucleic acid. The method can comprise or consist essentially of (a) contacting a sample with (i) a ribonucleoprotein comprising a deactivated RNA-guided nuclease and a guide RNA (gRNA) configured to bind to a target nucleic acid, wherein the deactivated RNA-guided nuclease comprises a biochemical tag at its N-terminus and C-terminus; and (ii) a comprising a plurality of moieties capable of binding to the biochemical tag; (b) incubating the contacted sample under conditions that promote binding of detectable label to the biochemical tag and binding of the ribonucleoprotein to the target nucleic acid; whereby an interconnected network of detectable labeled ribonucleoprotein-target nucleic acid complexes is formed; (c) isolating labeled ribonucleoprotein-target nucleic acid complexes of the interconnected network; and detecting the detectable label or a target nucleic acid of an isolated ribonucleoprotein-target nucleic acid complex, thereby indicating the presence of the target nucleic acid in the sample. The detectable label can comprise a fluorophore. Isolating can comprise silica-based chromatography. The biochemical tag can be biotin and the detectable label can comprise a plurality of streptavidin moieties. Silica-based chromatography can comprise (a) contacting an interconnected network of fluorophore-labeled ribonucleoprotein-target nucleic complexes to a silica or silica-like substrate; (b) washing the contacted substrate using a wash buffer comprising sodium chloride (NaCl), ammonium acetate, and one or more of L-arginine, L-lysine, and isopropyl alcohol; and (c) eluting labeled streptavidin ribonucleoprotein-target nucleic acid complexes from the washed substrate. Eluting can comprise contacting the washed, contacted substrate to an elution buffer comprising one or more of L-arginine, L-lysine, isopropyl alcohol, and a detergent. The detectable label can be a plurality of streptavidin-functionalized quantum dots, each comprising at least one fluorophore. The deactivated RNA-guided nuclease can be a deactivated Cas9. The method can further comprise, prior to the contacting step (a), the step of performing isothermal amplification of target nucleic acids in the sample. Isothermal amplification can comprise a primer set comprising any one of SEQ ID NOs: 1-54. Isothermal amplification can comprise reverse transcription loop-mediated isothermal amplification (RT-LAMP). The target nucleic acid can be a viral nucleic acid.

In a further aspect, provided herein is a method for detecting a target nucleic acid in a sample using a ribonucleoprotein which specifically binds the target nucleic acid and using a silica-based purification step to isolate a ribonucleoprotein bound to the target nucleic acid. The method can comprise or consist essentially of (a) incubating the sample with a ribonucleoprotein comprising a deactivated RNA-guided nuclease and a gRNA configured to bind to the target nucleic acid, wherein the deactivated RNA-guided nuclease comprises a detectable label or is bound by a monovalent detectable label, under conditions that promote binding of the deactivated RNA-guided nuclease and a guide RNA to the target nucleic acid; whereby a labeled ribonucleoprotein-target nucleic acid complex is formed; (b) contacting the labeled ribonucleoprotein-target nucleic complex to a silica or silica-like substrate, wherein the silica or silica-like substrate is equilibrated using an equilibration buffer comprising water, NaCl, ammonium acetate, and one or more of L-arginine and L-lysine; (c) washing the contacted silica or silica-like substrate using a wash buffer comprising water, NaCl, ammonium acetate, and isopropyl alcohol and one or more of L-arginine and L-lysine; and (d) eluting the labeled ribonucleoprotein-target nucleic acid complex from the washed substrate, thereby isolating the labeled ribonucleoprotein-target nucleic acid complex with reduced dissociation relative to isolation of labeled ribonucleoprotein-target nucleic acid complex using a silica or silica-like substrate in the absence of using the equilibration buffer and the wash buffer. Eluting can comprise contacting the washed, contacted substrate to an elution buffer comprising water and one or more of L-arginine, L-lysine, isopropyl alcohol, and a detergent; and optionally wherein the elution buffer comprises NaCl, ammonium acetate, and between 0.01% and 0.1% polysorbate-20. The equilibration buffer can comprise water, between 1.5 and 3 M NaCl, 10 mM ammonium acetate (pH 5.5), and one or more of the following: 1 M L-arginine, 1 M L-lysine, between 15% and 30% ethanol, and between 5% and 15% isopropyl alcohol. The wash buffer can comprise 1 M NaCl, 10 mM ammonium acetate (pH 5.5), and one or more of the following: 1 M L-arginine, 1 M L-lysine, between 5% and 15% isopropyl alcohol, and polysorbate-20. The method can further comprise, prior to the contacting step (a), performing isothermal amplification of target nucleic acids in the sample. Isothermal amplification can comprise a primer set comprising any one of SEQ ID NOs: 1-54. Isothermal amplification can comprise reverse transcription loop-mediated isothermal amplification (RT-LAMP). The target nucleic acid can be a viral nucleic acid.

In another aspect, provided herein is a composition comprising a nucleic acid selected from: a guide RNA (gRNA) comprising the nucleic acid the any one of SEQ ID NOs: 56-66 and a set of primers comprising the nucleic acids selected from: (a) SEQ ID NOs: 1-6 or six primers having at least 85%, 87%, 90%, 92%, 95%, 97%, or 98% identity thereto; (b) SEQ ID NOs: 7-11 or five primers having at least 85%, 87%, 90%, 92%, 95%, 97%, or 98% identity thereto; (c) SEQ ID NOs: 12-17 or six primers having at least 85%, 87%, 90%, 92%, 95%, 97%, or 98% identity thereto; (d) SEQ ID NOs: 18-22 or five primers having at least 85%, 87%, 90%, 92%, 95%, 97%, or 98% identity thereto; (e) SEQ ID NOs: 23-28 or six primers having at least 85%, 87%, 90%, 92%, 95%, 97%, or 98% identity thereto; (f) SEQ ID NOs: 29-34 or six primers having at least 85%, 87%, 90%, 92%, 95%, 97%, or 98% identity thereto; (g) SEQ ID NOs: 35-39 or five primers having at least 85%, 87%, 90%, 92%, 95%, 97%, or 98% identity thereto; (h) SEQ ID NOs: 40-43 or four primers having at least 85%, 87%, 90%, 92%, 95%, 97%, or 98% identity thereto; (i) SEQ ID NOs: 44-49 or six primers having at least 90% or 95% identity thereto; and (j) SEQ ID NOs: 50-54 or five primers having at least 90% or 95% identity thereto.

In another aspect, provided herein is a kit comprising a silica or silica-like substrate, an equilibration buffer, a wash buffer, and an elution buffer, wherein the equilibration buffer comprises water, between 1.5 M and 3 M NaCl, 10 mM ammonium acetate (pH 5.5), and one or more of the following: 1 M L-arginine, 1 M L-lysine, between 15% and 30% ethanol, and between 5% and 15% isopropyl alcohol; wherein the wash buffer comprises water, 1 M NaCl, 10 mM ammonium acetate (pH 5.5), and one or more of the following: 1 M L-arginine, 1 M L-lysine, and between 5% and 15% isopropyl alcohol; and wherein the elution buffer comprises water, NaCl, ammonium acetate, and one or more of L-arginine, L-lysine, isopropyl alcohol, and a detergent. The kit can further comprise instructions for isolating ribonucleoprotein-target nucleic acid complexes by contacting a sample comprising ribonucleoprotein-target nucleic acid complexes to the silica or silica-like substrate and using the equilibration buffer, wash buffer, and elution buffer to isolate ribonucleoprotein-target nucleic acid complexes from the silica or silica-like substrate with reduced dissociation of the complexes relative to isolation in the absence of the equilibration buffer, wash buffer, and/or elution buffer. The kit can further comprise a composition comprising a nucleic acid described herein.

DETAILED DESCRIPTION

Figure 1:
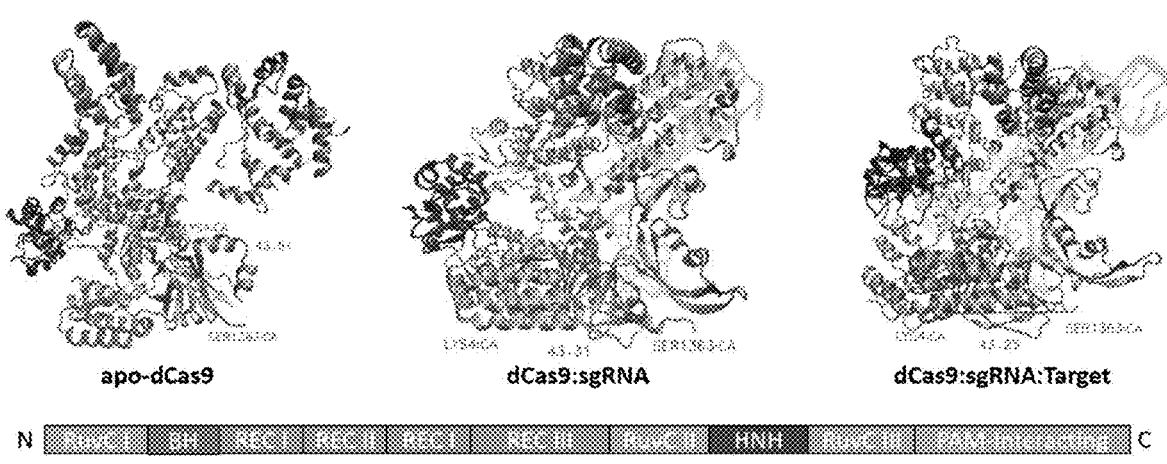
FIG. 1 illustrates three archetypal states of dCas9: apo-dCas9 (unprogrammed, no target), dRNP (dCas9+guide RNA), and dRNP-target (dCas9+guide RNA+specific target).

Provided herein are methods and compositions for isolating target specific nucleic acid-protein complexes from a sample and detecting target nucleic acids. The methods and compositions provided herein are based at least in part on the inventors' development of methods of isolating ribonucleoprotein-target nucleic acid complexes with reduced dissociation compared to conventional approaches. In some embodiments, the methods comprise a silica-based molecular separation, such as a silica-based nucleic acid adsorption technique.

In a first aspect, provided herein is a method for detecting a target nucleic acid in a sample using a ribonucleoprotein which specifically binds the target nucleic acid. The method may optionally comprise the formation of an interconnected network of detectable ribonucleoprotein-target nucleic acid complexes. The method may optionally comprise a silica-based isolating step to isolate a ribonucleoprotein-target nucleic acid complex, whether alone or as part of an interconnected network. The methods and compositions of this disclosure may be performed by isothermal amplification (e.g. LAMP or RT-LAMP) instead of conventional methods such as quantitative PCR (qPCR) after reverse transcription. The present methods and compositions are capable of providing fast and sensitive results without requiring expensive instrumentation, such as a PCR machine, or centralized laboratory, such as staffed with highly trained technicians.

In some embodiments, the method for detecting a target nucleic acid in a sample comprises the following steps: (a) contacting a sample with (i) a "dRNP" ribonucleoprotein comprising a deactivated RNA-guided nuclease and a guide RNA (gRNA) configured to bind to a target nucleic acid, wherein the deactivated RNA-guided nuclease comprises a biochemical tag at its N-terminus and C-terminus; and (ii) a "multivalent" detectable label comprising a plurality of moieties capable of binding to the biochemical tag; (b) incubating the contacted sample under conditions that promote binding of the detectable label to the biochemical tag and binding of the ribonucleoprotein to the target nucleic acid, if present in the sample; whereby an interconnected network of labeled ribonucleoprotein-target nucleic acid complexes (labeled "dRNP-target complexes") is formed; and (c) isolating labeled dRNP-target complexes of the interconnected network, thereby detecting the presence of a target nucleic acid in the sample. In some embodiments, the detectable label comprises a fluorophore. In some embodiments, the deactivated RNA-guided nuclease is a CRISPR-associated (Cas) protein comprising one or more mutations. In some embodiments, the biochemical tag comprises biotin and the detectable label comprises a plurality of avidin or streptavidin moieties.

In some embodiments, the method for detecting a target nucleic acid in a sample involves fluorescent signal amplification. For example, some embodiments comprise incubating the contacted sample under conditions that promote multivalent binding to create a network or web of linked fluorescent ribonucleoprotein-target nucleic acid complexes. The method may comprise contacting a sample with a recombinant deactivated Cas nuclease and a target-specific gRNA in the presence of streptavidin-functionalized fluorophore quantum dots under conditions in which the dCas and gRNA form a complex with the target nucleic acid (dRNP-target complex), and then isolating dRNP-target complexes using a chromatography method to detect a target nucleic acid in the sample.

As used herein, the terms "nucleic acid of interest," and "target nucleic acid" include a nucleic acid originating from one or more biological entities within a sample. The target nucleic acid of interest to be detected in a sample can be a sequence or a subsequence from DNA, such as nuclear or mitochondrial DNA, or cDNA that is reverse transcribed from RNA in the sample. The sequence of interest can also be from RNA, such as mRNA, rRNA, tRNA, miRNA, siRNAs, antisense RNAs, or long noncoding RNAs. More generally, the sequences of interest can be selected from any combination of sequences or subsequences in the genome or transcriptome of a species or an environment. In some cases, a defined set of primers are designed to amplify in a LAMP reaction target nucleic acid that would be expected in a sample, for example a gene or mRNA.

The term "detecting," "detect" or "detection" as used herein indicates the determination of the existence or presence of a target molecule or signal in a limited portion of space, including but not limited to a sample, a reaction mixture, a molecular complex and a substrate including a platform and an array. Detection is "quantitative" when it refers, relates to, or involves the measurement of quantity or amount of the target molecule or signal (also referred to as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified. An "optical detection" indicates detection performed through a detectable light signal(s): fluorescence, spectra, or images of an isolated or eluted labeled ribonucleoprotein-target nucleic acid complex.

As used herein, the term "detectable" means the label, molecule or atom can be detected by a known process, whether directly or indirectly, such as, after a processing step, chemical reaction, enzymatic reaction, and/or the addition of an additional reagent(s). For example, a "detectable label" is a label or molecule which can be detected by a known process, whether directly or indirectly. A detectable label may be detected, for example by ELISA, spectrophotometry, flow cytometry, or microscopy. For example, a label can be attached to a nucleic acid molecule or protein (indirectly or directly), thereby permitting detection of the nucleic acid molecule or protein. Examples of labels include, but are not limited to radioactive isotopes, enzyme substrates, co-factors, ligands, chemiluminescent agents, fluorophores, haptens, enzymes, and combinations thereof.

Methods for labeling and guidance in the choice of labels appropriate for various purposes are discussed, for example, in Sambrook, J. and Russell, D., editors. 2001. *Molecular Cloning: A Laboratory Manual* (3$^{rd}$ ed., Cold Spring Harbor Laboratory Press, NY) and Ausubel, F. et al., editors. 1988. *Current Protocols in Molecular Biology* (John Wiley & Sons, NY). Non-limiting examples of detectable labels include fluorophores, colorimetric agents, dyes, biochemical affinity tags, and bioluminescent agents that are suitable for functionalization, e.g., to an affinity tag cognate partner like biotin or streptavidin.

The sample may be a biological sample or non-biological sample. Non-limiting examples of samples include diagnostic tissue samples, blood, plasma, saliva, urine, environmental samples, food or water samples, agricultural products, and nucleic acid extracts of any of the aforementioned. The sample type may vary depending on the target nucleic acid of interest.

The methods of this disclosure can be performed using a sample of or from any biological entity, including without limitation one or more organisms, humans, non-human mammals, cells, bacteria, fungi, algae, or viruses. The term "sample" includes all types of tissue samples taken from a subject, such as, e.g., animal or plant tissue, buccal smears, samples obtained from biopsy or bodily fluids (e.g., blood, mucus, saliva, sputum, urine, amniotic fluid, etc.).

The methods of this disclosure can be performed using a sample which is a biological sample obtained from an individual subject (e.g., a human subject, a non-human mammalian subject) or a collection of subjects. A subject of the current disclosure includes a prokaryote, eukaryote, alga, fungus, plant, virus, and species of Metazoa. The term "subject" may be used interchangeably with the terms "individual" and "patient" and includes human and non-human subjects. In some embodiments, the subject is a mammal, such as a domesticated or pet mammal.

The methods of this disclosure can be performed using a sample which is non-biological either in whole or in part. Non-biological samples include, without limitation, clothing fibers, paper, plastic and packaging materials, swabs of objects and surfaces, and nucleic acid extracts of any of the aforementioned. In some cases, samples are obtained by swabbing, washing, or otherwise collecting biological material from a non-biological object such as a medical device, medical instrument, handrail, doorknob, etc.

The sample is, in some embodiments, a diagnostic sample. The biological sample can be saliva, a nasopharyngeal swab, blood, serum, sputum, or another matrix. For example, a diagnostic sample for detecting viruses, such as a SARS-CoV-2 variant, can be a saliva sample, a mucus sample, a nasopharyngeal swab sample, a sputum sample, or a blood sample.

Samples may be prepared for use as nucleic acid templates in the methods of this disclosure using conventional techniques, for example, a nucleic acid extraction. A sample comprising nucleic acids may be prepared from samples using conventional techniques, which typically depend on the source from which a sample is taken, including but not limited to a simple nucleic acid extraction comprising a cell lysis step, a centrifugation step to remove cellular debris, a proteolytic step to degrade proteins, an organic solvent precipitation step to remove proteins (e.g. using phenol or a mixture of phenol and chloroform), and a nucleic acid precipitation step using an alcohol (e.g. ethanol or isopropanol). Alternative nucleic acid sample preparation methods known in the art include silica-based methods for nucleic acid adsorption (e.g. silica membranes, beads or particles), magnetic-based solid support technologies (e.g. magnetic beads), anion exchange methods, and chromatographic methods using different resins. In some embodiments, the nucleic acid template sample is first prepared using a reverse transcriptase reaction known in the art. In some cases, the sample comprising nucleic acids undergoes no preparation step, i.e. a raw sample. In some cases, samples are heated prior to performing the other method steps. For instance, samples can be heated at a temperature of about 65° C. or greater, which kills the virus and releases nucleic acids. In other cases, samples are frozen (e.g., at −80° C.) prior to performing the other method steps.

A deactivated RNA-guided nuclease is a nuclease protein which is a nuclease guided by an RNA but is deactivated meaning the nuclease enzymatic or catalytic activity is inactive, dead, or significantly impaired. Non-limiting examples of RNA-guided nucleases include engineered CRISPR-associated (Cas) proteins, RNA interference proteins, and ribozymes. A deactivated RNA-guided nuclease can be synthesized, generated in vitro, or expressed in vivo using recombinant technology. As used herein, a "deactivated RNA-guided nuclease" has an amino-terminus ("N-terminus") and a carboxy-terminus ("C-terminus").

As used herein, the term "guide RNA" (gRNA) is an RNA that guides a deactivated RNA-guided nuclease. A deactivated RNA-guided nuclease can bind a gRNA to form a ribonucleoprotein complex (RNP), and the gRNA sequence guides the RNP to bind a specific site(s) in a nucleic acid via gRNA pairing to a specific sequence. A gRNA can be synthesized, generated in vitro, or expressed in vivo. Because a gRNA can provide sequence specific binding to a dRNP, certain dRNPs can bind to certain target nucleic acids in a sample, e.g. an RNA or DNA of interest comprising a specific polynucleotide sequence.

As used herein, the term "dRNP" refers to a ribonucleoprotein comprising a deactivated (i.e., enzymatically inactive) RNA-guided nuclease and an RNA (e.g. a guide RNA). As used herein, the term "dRNP-target complex" refers to a complex comprising a dRNP bound to a target nucleic acid.

As used herein, a biochemical tag is a polypeptide sequence or non-proteinaceous moiety which allows for high affinity and specific binding to another agent. Non-limiting examples of biochemical tags include peptide and polypeptide affinity tags as well as chemical modifications providing attachments of non-protein moieties, such as, linker-tethered affinity tags. Non-limiting examples of biochemical tags include peptide tags (e.g. His, HA, FLAG, Myc, Strep), protein tags (e.g. GST, MBP, GFP, Fc), and non-protein ligands (e.g. biotin).

As used herein, an "interconnected network" or "web" of detectable labeled ribonucleoprotein-target nucleic acid complexes refers to a macromolecular complex comprising a plurality of labeled ribonucleoprotein-target nucleic acid complexes. An interconnected network of detectable labeled ribonucleoprotein-target nucleic acid complexes may comprise one or more "bridges" between two individual dRNP-target complexes comprising a detectable label or comprising a Qdot comprising two or more detectable labels.

As used herein, the term "isolated" means to separate something from at least some of the components with which it is associated, either partially or fully. As used herein, the term "isolating" regarding a labeled streptavidin ribonucleoprotein-target nucleic acid complex means the labeled streptavidin ribonucleoprotein-target nucleic acid complex has been substantially separated or purified away from other molecules in the sample, such as, e.g., other chromosomal and extra-chromosomal DNA and RNA, proteins, lipids, carbohydrates, and cell debris. Nucleic acid molecules and proteins that have been "isolated" may be understood to have been purified by standard purification methods. The term also embraces nucleic acid molecules and proteins prepared by recombinant expression or chemically synthesized in vitro.

An isolating step of the methods described may comprise contacting the dRNP-target complexes (in solution) to a solid phase matrix or a nitrocellulose membrane. In some embodiments, target nucleic acid is detected by detecting or measuring fluorescence. In some cases, fluorescence is measured directly via reflection fluorimetry.

In some embodiments, the sample is first prepared using a reverse transcriptase reaction known in the art, such as, e.g., to provide a DNA nucleic acid template for an isothermal amplification reaction.

In some embodiments, the interconnected network provides fluorescent signal amplification. In some embodiments, the deactivated RNA-guided nuclease is biotinylated at the N- and C-termini and can bind to multivalent streptavidin detectable fluorophore labels via the biotin-streptavidin interaction. In some embodiments, the multivalent streptavidin detectable fluorophore label is bound during the incubating step to a Qdot via a streptavidin moiety.

In some embodiments, the detectable label comprises a fluorophore and two or more avidin or streptavidin moieties. In some embodiments, the method for detecting a target nucleic acid in a sample comprises the following steps: (a) contacting a sample with (i) a dRNP ribonucleoprotein comprising a deactivated RNA-guided nuclease and a gRNA configured to bind to the target nucleic acid, wherein the deactivated RNA-guided nuclease comprises at least one biotin-ligase substrate peptide at its N-terminus and at least one biotin-ligase substrate peptide at its C-terminus; and (ii) a multivalent streptavidin-functionalized fluorophore comprising two or more streptavidin moieties; (b) incubating the contacted sample under conditions that promote binding of multivalent streptavidin-functionalized fluorophores to biotin-ligase substrate peptides and binding of the ribonucleoprotein to the target nucleic acid to form an interconnected network comprising a plurality of fluorophore-labeled ribonucleoprotein-target nucleic acid complexes (labeled dRNP-target complexes); and (c) isolating fluorophore-labeled ribonucleoprotein-target nucleic acid complexes of the interconnected network, thereby detecting the presence of target nucleic acid in the sample. Isolating can comprise silica-based chromatography. Silica-based chromatography can comprise (a) contacting the interconnected network of fluorophore-labeled ribonucleoprotein-target nucleic complexes to a silica or silica-like substrate; (b) washing the contacted substrate using a wash buffer comprising sodium chloride (NaCl), ammonium acetate, and one or more of L-arginine, L-lysine, and isopropyl alcohol; and (c) eluting labeled streptavidin ribonucleoprotein-target nucleic acid complexes from the washed substrate. Eluting can comprise contacting the washed, contacted substrate to an elution buffer comprising one or more of L-arginine, L-lysine, and a detergent. The method can further comprise, prior to the contacting step (a), the step of performing isothermal amplification of target nucleic acids in the sample. Isothermal amplification can comprise reverse transcription loop-mediated isothermal amplification (RT-LAMP). The plurality of streptavidin-functionalized fluorophores can comprise streptavidin-functionalized quantum dots.

In some embodiments, the deactivated RNA-guided nuclease is derived from a CRISPR-associated nuclease or Cas nuclease such as, e.g. a Cas9, Cas12, or Cas13 protein.

The clustered regularly interspaced short palindromic repeat (CRISPR)-associated Cas nucleases are a group of programmable ribonucleoproteins (RNPs) involved in adaptive bacterial immunity. Specific DNA and RNA target motifs of about twenty nucleotides (in most cases) are defined by a CRISPR RNA (crRNA) containing the target sequence and a transactivating crRNA (tracrRNA) of constant sequence which fold to form a stem-loop structure bound by the Cas nuclease. Cas nucleases can scan an entire genome sample for a target sequence that is complementary to a single-guide RNA molecule (sgRNA) within the dRNP by unwinding duplex DNA and binding upstream of a protospacer adjacent motif. A recombinant Cas nuclease RNP, programmed by a sgRNA, can be used for searching for a very specific target nucleic acid sequence in sample. The nuclease activity of a naturally occurring Cas nuclease RNP can be inactivated or inhibited such that a deactivated Cas nuclease RNP stops at its target nucleic acid sequence, thereby locking the RNP to its target nucleic acid (for e.g., forming an RNP-target complex).

In some embodiments, the deactivated RNA-guided nuclease is a CRISPR-associated nuclease or Cas nuclease which is deactivated. As used herein, a nuclease deficient Cas protein is denoted with a lowercase 'd' prefix, such as, for e.g., dCas9 or dCas12. As used herein, the term "dCas9" refers to a deactivated *S. pyogenes* Cas9 protein, and "dCas12" refers to a deactivated *F. novicida*. A non-limiting example of a dCas9 is a Cas9 protein comprising the mutations D10A and H840A located in the RuvC and HNH nuclease domains, respectively.

As used herein, the term gRNA encompasses an RNA that guides CRISPR-Cas DNA editing. CRISPR-Cas proteins can bind a gRNA to form an RNP, and the gRNA sequence guides the RNP to bind and cut a specific site(s) in nucleic acid via pairing to a specific sequence. A CRISPR-Cas gRNA has at least two forms: (1) a trans-activating CRISPR RNA (tracrRNA) plus a CRISPR RNA (crRNA) and (2) a single guide RNA (sgRNA) that consists of both the crRNA and tracrRNA as a single molecule. The crRNA and the tracrRNA can form a complex which acts as the gRNA for the Cas enzyme. A Cas nuclease can be artificially programmed by altering or selecting its cognate gRNA. For example, a tracrRNA, crRNA, or sgRNA can be designed to target an RNP to bind a specific nucleic acid sequence. In some embodiments, the gRNA comprises a synthetic trans-activating CRISPR RNA (tracrRNA) and a synthetic CRISPR RNA (crRNA) designed to target a nucleic acid sequence of interest. In some embodiments, the gRNA comprises a synthetic or expressed single guide RNA (sgRNA) that consists of both the crRNA and tracrRNA as a single construct designed to target a nucleic acid sequence of interest. A tracrRNA, crRNA, or sgRNA can be synthesized, generated in vitro, or expressed in vivo.

In some embodiments, the deactivated RNA-guided nuclease is a nuclease-activity deficient *S. pyogenes* Cas9 ("dCas9") protein complexed with a guide ribonucleic acid, such as a target-specific gRNA. dCas9 can specifically and stably bind to a target DNA sequence consisting of a 20-nucleotide recognition sequence ("spacer") upstream of a proto-adjacent spacer motif (PAM; NGG for *S. pyogenes*). Spacer specificity can be conferred by altering the spacer region of the single guide RNA (sgRNA) component of the dRNP binary complex. Guide RNA specificity can be validated by in vitro cutting of target DNA by a wildtype *S. pyogenes* Cas9 complex.

In some embodiments, the biochemical tag comprises a biotin, AviTag™, HaloTag®, or SNAP-Tag®. In some embodiments, the biochemical tag is a biotin tag and the detectable label comprises avidin and/or streptavidin. In some embodiments, the biochemical tag is an AviTag and the detectable label comprises SEQ ID NO:67; the biochemical tag is HaloTag and the detectable label comprises a chloroalkane; the biochemical tag is SNAP-tag and the detectable label comprises a guanine or chloropyrimidine; or the biochemical tag is CLIP-tag and the detectable label comprises a benzylcytosine.

As used herein, a "biotin tag" is a biotin moiety covalently attached to the deactivated RNA-guided nuclease. A highly selective and high affinity binding can occur between biotin and streptavidin (e.g., characterized by a dissociation constant (KD) of $10^{-14}$ M) which can tolerate stringent wash conditions. A biotin tag may be attached to a terminus of a deactivated RNA-guided nuclease using a biotinylation reaction wherein the deactivated RNA-guided nuclease comprises at least one biotin-ligase substrate region (e.g., a biotin-ligase substrate peptide) at either its N-terminus and/or C-terminus. A biotin-ligase substrate region is a polypeptide region of the deactivated RNA-guided nuclease which may be labeled with biotin using a biotinylation reaction catalyzed by BirA enzyme, or variant thereof, from *E. coli*. In some embodiments, the deactivated RNA-guided nuclease comprises dual biotinylation meaning both the N-terminus and C-terminus is covalently attached to a biotin tag.

A streptavidin-functionalized detectable label is a detectable label which is physically coupled to streptavidin such that the streptavidin is capable of binding to biotin and the label can be detected. A multivalent streptavidin detectable label is a molecule comprising a detectable label and two or more streptavidin moieties.

In some embodiments, the biochemical tag is considered a self-labeling enzyme so long as the enzyme provides high affinity and specific binding to another agent. In some embodiments, the biochemical tag is an affinity tag added by a self-labeling enzyme incorporated into the N- and/or C-terminals of the deactivated RNA-guided nuclease. For example, a modified BirA enzyme tag called a biotin-ligase can be used to self-label a protein with a biotin tag.

An AviTag™ is a self-labeling polypeptide tag comprising polypeptide of about fifteen amino acids (e.g. GLN-DIFEAQKIEWHEA (SEQ ID NO: 67)) that forms covalent attachments to an AviTag™ substrate (e.g. a biotin moiety) at a specific lysine residue.

A SNAP-Tag® is a self-labeling polypeptide tag comprising polypeptide of about 19 kDa derived from human $O^6$-alkylguanine-DNA-alkyltransferase that forms covalent attachments to a SNAP-Tag® substrate (e.g. a moiety comprising a guanine or chloropyrimidine). A CLIP-Tag™ is subtype of SNAP-Tag® which accepts $O^2$-benzylcytosine derivatives as substrates (e.g. CLIP-Tag™ substrates).

A HaloTag® is a self-labeling polypeptide tag comprising a polypeptide of about 33 kDa that is a mutagenized haloalkane dehalogenase that forms covalent attachments to substituted chloroalkane substrates, such as, one having a derivatized functional group (e.g. a Halo-Ligand). Commercially available Halo-ligand derivatives include the invariant chloroalkane moiety followed by four ethylene glycol repeats, and a reactive sulfahydryl, succinimidyl ester, amine, or iodoacetamide group, among many other options.

In some embodiments, the CRISPR-associated (Cas) nuclease is a nuclease-deficient Cas9 (dCas) engineered to express biotin-ligase substrate peptides at the N- and C-terminals. The preferred embodiment may comprise an engineered nuclease-deficient Cas9 (dCas) having a biotin-tag at both the N- and C-termini, having been at least 90% double-biotinylated in vitro via the activity of recombinant BirA holoenzyme, and showing appreciable activity when incubated with a gRNA and specific target DNA under buffered conditions. While the aforementioned example is given for dCas9, the skilled worker will recognize that other deactivated Cas proteins can be used according to these methods for detection of a specific DNA or RNA target nucleic acid. For instance, in other embodiments, the dCas12 is a nuclease-deficient Cas12 protein engineered to comprise an AviTag™, biotin tag, HaloTag®, and/or a SNAP-Tag® (e.g. a CLIP-Tag™) at its N- and C-terminals.

Any appropriate detectable label can be used according to the methods of this disclosure so long as the detectable label can be detected by a known process. In some embodiments, the detectable label generates a color, fluorescent, or luminescent signal. In some embodiments, the detectable label is capable of generating a detectable signal, such as, e.g., a specific emission spectrum upon excitation. In some embodiments, the detectable label comprises a plurality of moieties capable of binding to a biochemical tag (sometimes referred to herein as multivalent). In some embodiments, the detectable label is preattached to a deactivated RNA-guided nuclease prior to a contacting step. In other embodiments, the detectable label is capable of binding to a deactivated RNA-guided nuclease during a contacting step. In some further embodiments, the detectable label is only capable of binding to one deactivated RNA-guided nuclease at a time (sometimes referred to herein as monovalent).

In some embodiments, the detectable label comprises a colorimetric agent. In some embodiments, the colorimetric label is a chromoprotein which exhibits a visible color. Illustrative but non-limiting examples of chromoproteins include meffRed, eforRed, asPink, spisPink, scOrange, fwYellow, amilGFP, amajLime, cjBlue, meffBlue, aeBlue, amilCP, tsPurple, and gfasPurple.

In some embodiments, the detectable label comprises a fluorophore. As used herein, the term "fluorophore" includes a molecule that absorbs a photon of a wavelength and emits a photon of another wavelength. The term "fluorophore" includes but is not limited to Alex Fluor dyes, diAcFAM, fluorescent proteins (e.g. GFPs, RFPs, CFPs, and YFPs), fluorophore quantum dots (e.g. fluorescent quantum dot nanocrystals (Qdots)), fluorescein, coumarin, fluorescein isothiocyanate (FITC), Oregon green, (TMR), tetramethyl-rhodamine (TRITC), and upconversion phosphors (UCNPs). The term "fluorophore" also refers to a moiety that is inherently fluorescent or demonstrates a change in fluorescence upon binding to a biological compound or metal ion, or metabolism by an enzyme (i.e., fluorogenic). Fluorophores may be substituted to alter the solubility, spectral properties, or physical properties of the fluorophore. Numerous fluorophores are known to those skilled in the art and include, without limitation, coumarins, acridines, furans, dansyls, cyanines, pyrenes, naphthalenes, benzofurans, quinolines, quinazolinones, indoles, benzazoles, borapolyazaindacene, oxazines and xanthenes, with the latter including fluoresceins, rhodamines, rosamines and rhodols. Exemplary fluorophores for compositions of this disclosure include, without limitation, fluorescein, FAM (6-fluorescein amidite), PE-Cy5.5, sulforhodamine 101, pyrenebutanoate, acridine, ethenoadenosine, eosin, rhodamine, 5-(2'-aminoethyl)aminonaphthalene (EDANS), fluorescein isothiocyanate (FITC), N-hydroxysuccinimidyl-1-pyrenesulfonate (PYS), tetramethylrhodamine (TAMRA), Rhodamine X, Cy5, and erythrosine.

Figure 2:
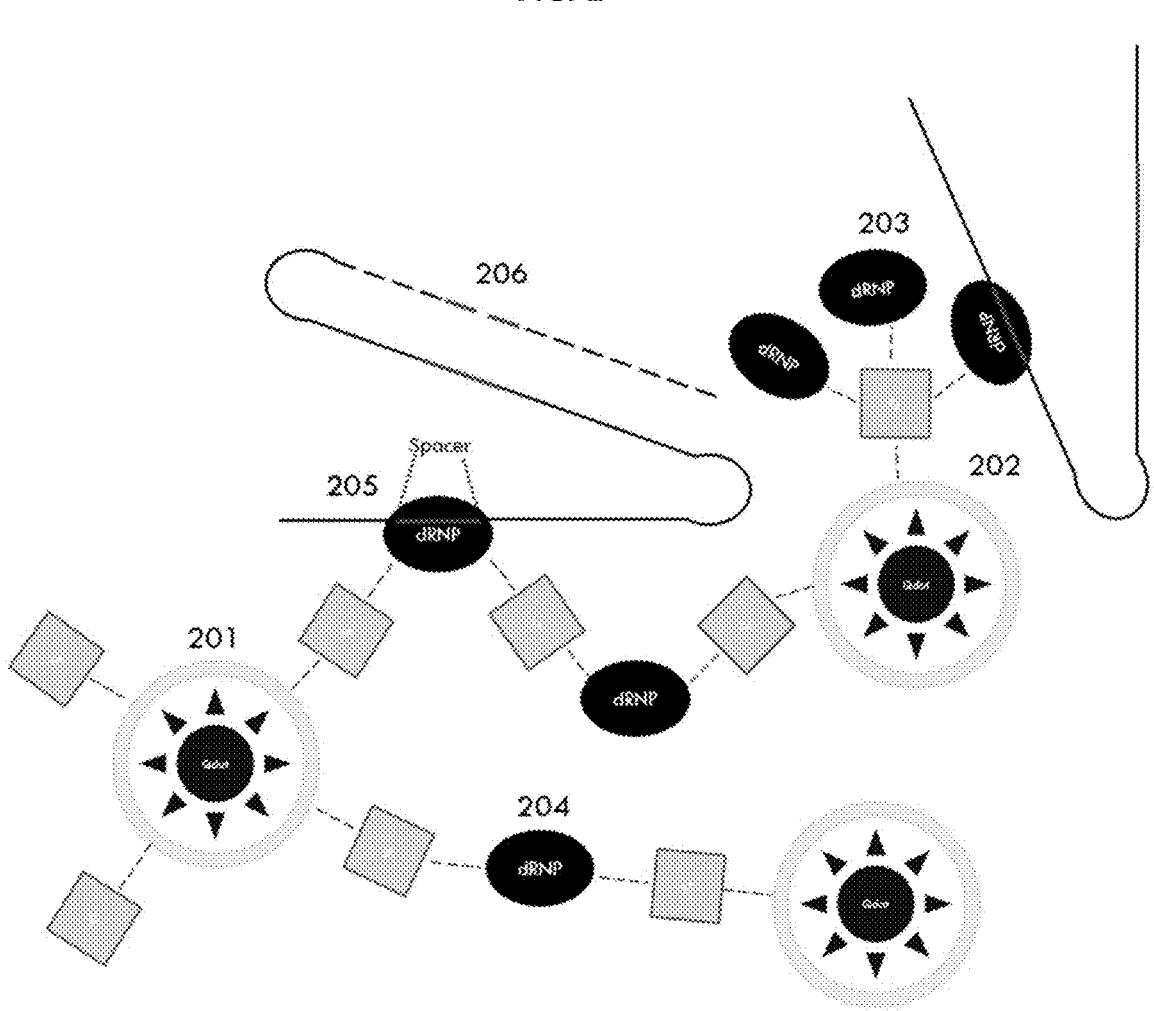
FIG. 2 illustrates "web" fluorescent amplification resulting from interactions between streptavidin-functionalized fluorescent Qdots, N- and C-terminus tagged dRNPs, and target DNA.

In some embodiments, the detectable label can bind to a quantum dot or is part of a quantum dot during an incubating step. In some further embodiments, the detectable label comprises a streptavidin-functionalized fluorophore. For example, streptavidin-functionalized quantum dot nanocrystals ("Qdots") can be used for the methods of this disclosure. Referring to FIG. 2, streptavidin-functionalized quantum dot nanocrystals such as qDot 655 and qDot 605 (201) can be used in low molar concentrations relative to dCas9, which promotes multivalent binding of each qDot to several dCas9 molecules (202). Fluorescent Qdots typically have between 5 and 10 streptavidin proteins per nanocrystal, and each streptavidin can bind between 1-4 targets (203), allowing a highly networked intermolecular structure to emerge. In this manner, a highly networked intermolecular structure ("web") of fluorescent dCas9-target DNA complexes will form. Advantageously, bound dCas9 can, in turn, bind to other Qdots and act as a bridge between nanocrystals but also serve as a bridge between the nanocrystal complex and multiple target DNAs (204). In the presence of a target nucleic acid, Qdot-bound dCas9 molecules of the web can serve as attachment sites for the target DNA (205). The incorporation of unbound dCas9 molecules as bridges is beneficial as the high surface area of the "web" may bring the dCas9 into closer contact with unbound target DNAs.

Reverse Transcription and Isothermal Amplification of Target Nucleic Acids in Clinical Samples In some embodiments, the method comprises, in a first step, performing an isothermal amplification reaction to amplify a target nucleic acid of interest. In some embodiments, the method comprises, in a first step, performing a reverse transcription reaction and/or an isothermal amplification reaction to amplify a target nucleic acid of interest. In some embodiments, the isothermal amplification reaction is a loop-mediated isothermal amplification (LAMP) reaction. In some embodiments, the isothermal amplification reaction comprises a reverse transcriptase or is preceded by a reverse transcription reaction. In some embodiments, the isothermal amplification reaction is a loop-mediated isothermal amplification (LAMP) reaction which comprises a reverse transcriptase or reverse transcription step (RT-LAMP).

Reverse transcription is a process of generating complementary DNA (cDNA) molecules from an RNA template using an RNA-dependent DNA polymerase. In some cases, the cDNA is subsequently amplified using PCR or isothermal amplification.

As used herein, a "LAMP reaction" refers to a loop mediated isothermal amplification (LAMP) reaction. Typically, a LAMP reaction takes about 20 minutes to about one hour and is performed at a set temperature between 60-85° C. to optimize template melting and primer annealing. Typically, a LAMP reaction comprises (1) a thermostable strand displacing polymerase, (2) a sample comprising nucleic acid (e.g. a RNA or DNA nucleic acid template), (3) at least four or more sequence specific primers, (4) nucleotide triphosphates, (5) a divalent metal ion (e.g. $Mg^{+2}$), and (6) a buffer. Some LAMP reactions further comprise a detectable agent, such as, e.g., a dye or nucleic acid probe.

The term "LAMP primer set" refers to a set of four, five, six or more LAMP primers which is capable (under optimized conditions) of producing a LAMP reaction product when a target nucleic acid template is present in the reaction (e.g. temperature and template concentration). In some embodiments, a LAMP primer set comprises two inner primers (FIP and BIP) and two outer primers (F3 and B3). In other embodiments, a LAMP primer set comprises two inner primers (FIP and BIP), two outer primers (F3 and B3), and two loop primers (LF and LB).

In some embodiments, the method comprises an isothermal amplification reaction to amplify target nucleic acids of interest. For instance, isothermal amplification can be performed to amplify target nucleic acids, such as nucleic acids of a pathogen (e.g., virus, bacterium) in a sample obtained from a subject. Any isothermal amplification protocol can be used according to the methods provided herein. Other isothermal amplification methods include, without limitation, strand displacement amplification (SDA), helicase displacement amplification (HDA), nicking enzyme amplification reaction (NEAR), signal mediated amplification of RNA technology (SMART), loop-mediated isothermal amplification (LAMP), rolling circle amplification (RCA), isothermal multiple displacement amplification (IMDA), single primer isothermal amplification (SPIA), recombinase polymerase amplification (RPA), and RT-RPA, RT-HAD.

In some cases, the isothermal amplification method is an RT-LAMP, in which target RNA nucleic acids in a sample are amplified into cDNA molecules, and the amplified cDNA molecules are amplified into double-stranded DNA (dsDNA). In some embodiments, the isothermal amplification reaction is RT-LAMP, performed using primer pairs that flank a nucleic acid region of interest. When the target nucleic acid is a viral nucleic acid, genomic sequence information for the virus of interest can be used to design primers 5' and 3' to the nucleic acid region of interest.

In some cases, the target nucleic acid is a viral nucleic acid. For example, the target nucleic acid can be a nucleic acid from a virus such as a virus associated with human disease. Exemplary viruses include, without limitation, SARS-2-CoV, Influenza A, and Human HPV. As used herein, the term "SARS-2-CoV" may be interchangeable with "SARS-CoV-2."

Listed in Table 1 below are the polynucleotide sequences of primer sets for the amplification and fluorescent and/or colorimetric detection of SARS-CoV-2 from synthetic RNA and heat-inactivated viral sample templates obtained from saliva. The positive control LAMP primer sets for detecting human 18S rRNA sequences shown in Table 2 or for detecting human beta-actin ACTB sequences shown in Table 3 may be used in conjunction with the methods described herein. Additional primers known in the art, may be used in conjunction with the methods described herein. The primer sets in Tables 1-3 may be used in a method and/or kit described herein.

TABLE 1

| Illustrative Primer Sets for Detecting SARS-CoV-2 Nucleic Acids |  |
| --- | --- |
| Primer | Sequence |
| Primer Set for detecting SARS-CoV-2 Spike ORF | |
| Spike_002-F3 | ACAATTTGGCAGAGACATTG (SEQ ID NO: 1) |
| Spike_002_B3 | CAAGTAGGAGTAAGTTGATCTG (SEQ ID NO: 2) |
| Spike_002_FIP | GACACCACCAAAAGAACATGGTGCTGACACTACTGATGCTGTC (SEQ ID NO: 3) |
| Spike_002_BIP | CCAGGAACAAATACTTCTAACCAGGTGAATAGCAACAGGGACTT (SEQ ID NO: 4) |
| Spike_002_LF | TGTCAAGAATCTCAAGTGTCTGTG (SEQ ID NO: 5) |
| Spike_002_LB | CTTTATCAGGATGTTAACTGCACAG (SEQ ID NO: 6) |
| Primer Set for detecting SARS-CoV-2 ORF1ab | |
| ORF1ab_001_F3 | GGCTAACTAACATCTTTGGC (SEQ ID NO: 7) |
| ORF1ab_001_B3 | GTCAGCACACAAAGCCAA (SEQ ID NO: 8) |
| ORF1ab_001_FIP | GTCTCTAAGAAACTCTACACCTTCCTGTTTATGAAAAACTCAAACCCG (SEQ ID NO: 9) |
| ORF1ab_001_BIP | TATCTCAACCTGTGCTTGTGAAAAGAATGTCTGAACACTCTCCT (SEQ ID NO: 10) |
| ORF1ab_001_LB | ACAAATTGTCACCTGTGCAAAGGA (SEQ ID NO: 11) |
| Primer Set for detecting SARS-CoV-2 N2 ORF | |
| N2_001-F3 | CCCCGCATTACGTTTGGT (SEQ ID NO: 12) |
| N2_001-B3 | AGCCAATTTGGTCATCTGGA (SEQ ID NO: 13) |
| N2_001-FIP | GTTGTTTTGATCGCGCCCCACGGACCCTCAGATTCAACTGG (SEQ ID NO: 14) |
| N2_001-BIP | CGTCTTGGTTCACCGCTCTCATGGTGTTAATTGGAACGCCT (SEQ ID NO: 15) |
| N2_001-LF | GCGTTCTCCATTCTGGTTACTG (SEQ ID NO: 16) |
| N2_001-LB | CTCAACATGGCAAGGAAGACC (SEQ ID NO: 17) |

TABLE 2

Illustrative Primer Set for Detecting 18S
Ribosomal RNA Sequences

| Primer | Sequence |
| --- | --- |
| Primer Set for detecting human 18S rRNA | |
| 188_TRNA-F3 | TGGTGGAGCGATTTGTCTG (SEQ ID NO: 18) |
| 18S_rRNA-B3 | TGAGCCAGTCAGTGTAGCG (SEQ ID NO: 19) |
| 18S_rRNA-FIP | AAGAAGTTGGGGGACGCCGAACGAGACTCTGGCATG CTAA (SEQ ID NO: 20) |

TABLE 2-continued

Illustrative Primer Set for Detecting 18S
Ribosomal RNA Sequences

| Primer | Sequence |
| --- | --- |
| 18S_rRNA-BIP | GGACAAGTGGCGTTCAGCCAAGCCCCGGACATCTAA GG (SEQ ID NO: 21) |
| 18S_rRNA-LB | CCCGAGATTGAGCAATAACAGG (SEQ ID NO: 22) |

TABLE 3

Illustrative Primer Sets for Detecting ACTB Genetic Sequences

| Primer | Sequence |
| --- | --- |
| Primer Set #1 for detecting human ACTB ORF | |
| ACTB_001-F3 | GGCATCCACGAAACTACCTT (SEQ ID NO: 23) |
| ACTB_001-B3 | GCCGATCCACACGGAGTAC (SEQ ID NO: 24) |
| ACTB_001-FIP | TGCCGCCAGACAGCACTGTGTGAAGTGTGACGTGGACATC (SEQ ID NO: 25) |
| ACTB_001-BIP | TTGCCGACAGGATGCAGAAGGGCGCTCAGGAGGAGCAAT (SEQ ID NO: 26) |
| ACTB_001-LF | GGCGTACAGGTCTTTGCG (SEQ ID NO: 27) |
| ACTB_001-LB | CCCTGGCACCCAGCACAATG (SEQ ID NO: 28) |
| Primer Set #2 for detecting human ACTB ORF | |
| ACTB_002-F3 | GCGCGGCTACAGCTTCA (SEQ ID NO: 29) |
| ACTB_002-B3 | GGAAGAGTGCCTCAGGGC (SEQ ID NO: 30) |
| ACTB_002-FIP | AAGTCCAGGGCGACGTAGCACCGGCCGAGCGGGAAAT (SEQ ID NO: 31) |
| ACTB_002-BIP | GAGATGGCCACGGCTGCTTCCATTGCCAATGGTGATGACCT (SEQ ID NO: 32) |
| ACTB_002-LF | TTCTCCTTAATGTCACGCACG (SEQ ID NO: 33) |
| ACTB_002-LB | CCCTGGAGAAGAGCTACGAGC (SEQ ID NO: 34) |
| Primer Set #3 for detecting human ACTB ORF | |
| ACTB_003-F3 | CCCTGAAGTACCCCATCGA (SEQ ID NO: 35) |
| ACTB_003-B3 | TGGGGTGTTGAAGGTCTCAA (SEQ ID NO: 36) |
| ACTB_003-FIP | AGCCACACGCAGCTCATTGTAGCACGGCATCGTCACCAAC (SEQ ID NO: 37) |
| ACTB_003-BIP | AGCACCCCGTGCTGCTGAGTCATCTTCTCGCGGTTGG (SEQ ID NO: 38) |
| ACTB_003-LF | CCAGATTTTCTCCATGTCGTCC (SEQ ID NO: 39) |
| Primer Set #4 for detecting human ACTB ORF | |
| ACTB_004-F3 | TGCTGCTGACCGAGGC (SEQ ID NO: 40) |
| ACTB_004-B3 | GCACAGTGTGGGTGACC (SEQ ID NO: 41) |
| ACTB_004-FIP | ATGGCTGGGGTGTTGAAGGTCTCTGAACCCCAAGGCCAACC (SEQ ID NO: 42) |
| ACTB_004-BIP | TACGTTGCTATCCAGGCTGTGCCACCGGAGTCCATCACGA (SEQ ID NO: 43) |

In some cases, multiple primer pairs are used. As an example, multiple primers were designed to amplify a region of about 250 nucleotides of the SARS-2-CoV nucleocapsid gene in a RT-LAMP reaction (Table 4, provided in 5'→3' orientation). As a positive control, multiple primers were designed to target a region of similar length (approximately 250 nucleotides) of the human 18S RNA gene (Table 5, provided in 5'→3' orientation). Primers designed to amplify other housekeeping genes or other genes may be used as positive controls.

TABLE 4

| Primers for SARS-2-CoV nucleocapsid amplification |
| --- |
| N.F3: TGGACCCCAAAATCAGCG (SEQ ID NO: 44) |
| N.B3: AGCCAATTTGGTCATCTGGA (SEQ ID NO: 45) |
| N.FIP: GTTGTTTTGATCGCGCCCCACATTACGTTTGGTGGACCCTC (SEQ ID NO: 46) |
| N.BIP: ATACTGCGTCTTGGTTCACCGCATTGGAACGCCTTGTCCTC (SEQ ID NO: 47) |
| N.LF: CTGGTTACTGCCAGTTGAATCT (SEQ ID NO: 48) |
| N.LB: TCTCACTCAACATGGCAAGGAAG (SEQ ID NO: 49) |

TABLE 5

| Primers for positive control amplification |
| --- |
| 18s_rRNA-F3: TGGTGGAGCGATTTGTCTG (SEQ ID NO: 50) |
| 18s_rRNA-B3: TGAGCCAGTCAGTGTAGCG (SEQ ID NO: 51) |
| 18s_rRNA-FIP: AAGAAGTTGGGGGACGCCGAACGAGACTCTGGCATGCTAA (SEQ ID NO: 52) |
| 18s_rRNA-BIP: GGACAAGTGGCGTTCAGCCAAGCCCCGGACATCTAAGG (SEQ ID NO: 53) |
| 18s_rRNA-LoopB: CCCGAGATTGAGCAATAACAGG (SEQ ID NO: 54) |

Utilizing target-flanking primers, the target nucleic acid can be reliably amplified. In this example, the target sequence for detection is 5'-gggcgcgaucaaaacaacgu-3' (SEQ ID NO: 55), which corresponds to the N gene of SARS-2-CoV. The entire sgRNA sequence is gggcgcgaucaaaacaacgu-GUUUUAGAGCUA-GAAAUAGCAAGUUAAAAUAAGGCUAGUCC G (SEQ ID NO: 56), where lower case letters correspond to the spacer, and upper-case letters correspond to crRNA stem loops necessary for complexing to apo-dCas9. In this example, the primers amplified target nucleic acids of the sample to a yield of approximately 10-15 specific product from as little as 1-10 copies of viral RNA in 20-35 minutes, depending on the amount of input material.

It will be readily understood that other sequences can be targeted by designing different sgRNAs. By way of example, additional sequences within SARS-2-CoV Spike, Matrix, and RNA-dependent RNA polymerases (RdRp) can be targeted. Exemplary target sequences for detection (lowercase) and full sgRNA sequences (lowercase+uppercase) are shown below:

```
SARS-CoV-2 Spike 1:
                                      (SEQ ID NO: 57)
5' tctaaagccgaaaaaccctgGUUUUAGAGCUAGAAAUAGCAAGUUAA

AAUAAGGCUAGUCCG 3'

SARS-CoV-2 Spike 2:
                                      (SEQ ID NO: 58)
5' gctacactacgtgcccgccgGUUUUAGAGCUAGAAAUAGCAAGUUAA

AAUAAGGCUAGUCCG 3'

SARS-CoV-2 RdRP 1:
                                      (SEQ ID NO: 59)
5' agttgtggcatctcctgatgGUUUUAGAGCUAGAAAUAGCAAGUUAA

AAUAAGGCUAGUCCG 3'

SARS-CoV-2 Matrix 1:
                                      (SEQ ID NO: 60)
5' ttgcgcgtacgcgttccatgGUUUUAGAGCUAGAAAUAGCAAGUUAA

AAUAAGGCUAGUCCG 3'

SARS-CoV-2 Matrix 2:
                                      (SEQ ID NO: 61)
5' caatacgaagatgtccacgaGUUUUAGAGCUAGAAAUAGCAAGUUAA

AAUAAGGCUAGUCCG 3'
```

As another example, *Alicyclobacillus acidophilus* dCas12b was used to target Human Papilloma Virus (HPV) 16 and 18 sequences for discrimination of high-risk HPVs. Exemplary target sequences for detecting HPV16 and HPV18 nucleic acids are listed below:

```
HPV16 E6:
                                      (SEQ ID NO: 62)
gcaacagttactgcgacgtg;

HPV18 E2_1:
                                      (SEQ ID NO: 63)
aaatgttataggctggcacc;

HPV18 E2_2:
                                      (SEQ ID NO: 64)
acaagctgagtagcggatac;

HPV18 E6:
                                      (SEQ ID NO: 65)
ataaggtgcctgcggtgcca;

HPV18 L1:
                                      (SEQ ID NO: 66)
tggcggcctagtgacaatac.
```

In some embodiments, amplified products of RT-LAMP are direct inputs for detection using gene sequence-specific dRNPs. For instance, in some cases, dRNPs and Cas9 buffer solution are added directly to completed RT-LAMP reaction products and incubated for downstream analysis by isolating labeled dRNP-target complexes.

In another aspect, provided herein is an assay for the detection of viral nucleic acids in a biological sample obtained from a subject. In some embodiments, the biological samples are patient samples taken for diagnostic purposes. In such embodiments, isothermal amplification such as RT-LAMP is performed to amplify target RNA sequences of interest that may be present in the biological sample. As in the example above, primers are designed to flank and amplify a target region of interest for the virus of interest. Viral nucleic acids of interest can be nucleic acids of viruses such as, for example, SARS-2-CoV, Influenza A, and HPV. Because sequence information is known for a large number of viruses, particularly those associated with human diseases, it is well within the skill of a practitioner in the field to design appropriate primers to amplify nucleic acids of interest for a given target virus and biological sample type.

Formation of Fluorescent dCas9-Target DNA Webs Via Tetravalent Linkers

In some embodiments, dual biotinylation of dCas9 or another dCas nuclease at the N- and C-termini is exploited to amplify a fluorescent signal via the formation of intermolecular networks or webs comprising more than one fluorescent molecule per bound dCas molecule. Any appropriate fluorescent signal can be used according to the methods of this disclosure. In some embodiments, the fluorescent signal is provided by a detectable label comprising fluorophore and capable of binding to both of the dual biotinylation tags of a dCas protein.

In some embodiments, streptavidin-functionalized quantum dot nanocrystals ("Qdots") are used for the methods of this disclosure. Referring to FIG. 2, streptavidin-functionalized quantum dot nanocrystals such as qDot 655 and qDot 605 (201) can be used in low molar concentrations relative to dCas9, which promotes multivalent binding of each qDot to several dCas9 molecules (202). Fluorescent Qdots typically have between 5 and 10 streptavidin proteins per nanocrystal, and each streptavidin can bind between 1-4 targets (203), allowing a highly networked intermolecular structure to emerge. In this manner, a highly networked intermolecular structure ("web") of fluorescent dCas9-target DNA complexes will form. Advantageously, bound dCas9 can, in turn, bind to other Qdots and act as a bridge between nanocrystals but also serve as a bridge between the nanocrystal complex and multiple target DNAs (204). In the presence of a target nucleic acid, Qdot-bound dCas9 molecules of the web can serve as attachment sites for the target DNA (205). The incorporation of unbound dCas9 molecules as bridges is beneficial as the high surface area of the "web" may bring the dCas into closer contact with unbound target DNAs.

RT-LAMP reaction products are known to comprise a distribution of amplicon concatemers, the bulk of which are 1-7 sequential repeats of the target nucleic acid (206). Each repeat contains the target spacer, meaning that a single RT-LAMP amplification product can bind to several dRNPs. The prevalence of anchor points enhances the association between the fluorescent network (web) and the target DNA, while also increasing the chance that at least one dCas9 molecule will bind to each target nucleic acid. In this way, the method leverages two forms of signal amplification.

Isolation of Fluorescent DNA-dRNP Networks Via Silica-Like Surface Chemistry

In another aspect, provided herein are methods for isolating detectably labeled dCas9-target nucleic acid complexes using chromatography with silica, silica-based, or silica-like substrates.

Figure 3:
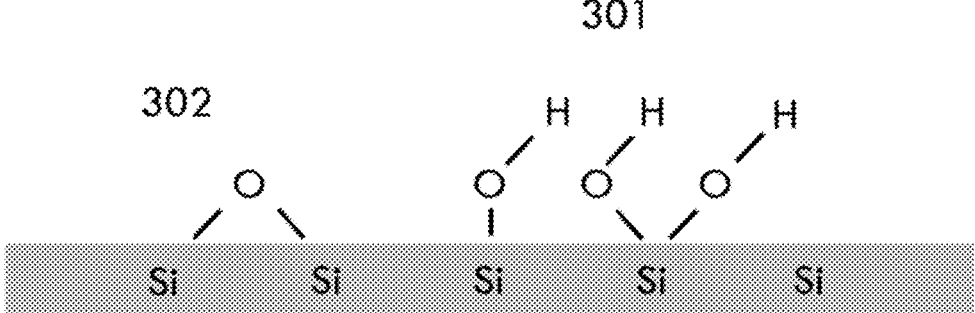
FIG. 3 illustrates silica surface chemistry at a pH 4 or a pH of about 8.5.
Figure 3:
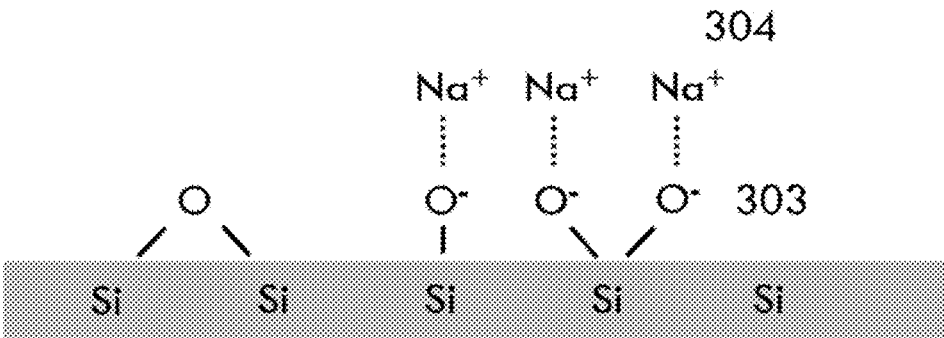

Referring to FIG. 3, at low pH values, silanols are reduced and have no net charge (302). However, as pH increases above the pKa of silanol (about 5.4), silanols become progressively more oxidized and negatively charged (301). At a pH of 7.5, about 50% of surface silanols will be oxidized. Bare oxidized silanols do not bind DNA due to the repulsive electrostatic interactions between the negative silanol and negatively charged phosphate backbone of DNA (pKa about 4.0).

In general, silica-based chromatography comprises binding nucleic acids to the surface of silica resin or membrane in the presence of a high concentration of chaotropic salts. Contaminants are washed away, and the nucleic acids are eluted from the silica-based resin or membrane in water or a low-salt buffer. The principle of silica-based nucleic acid isolation is based on the high affinity of the negatively charged nucleic acid backbone towards a positively charged silica surface under concentrated chaotropic salt conditions. While silica-based chromatography has been widely utilized to isolate and purify nucleic acid species for decades, the binding conditions under which DNA adsorbs to silica effectively are stringent and unamenable to retaining protein-DNA interactions such as dRNP-target complexes. Conventional silica-based DNA isolation strategies incorporate very high amounts of chaotropic salts such as guanidine-HCl which, in solution, are believed to have the capability to shield oxidized surface silanols (304) and form weak electrostatic connections to nucleic acids. High salt and low pH conditions permit adsorption of DNA to silica at high densities; however, these conditions also promote rapidly denaturation of the vast majority of proteins. Without being bound to any particular theory or mode of action, it is believed that the methods of this disclosure are improved relative to conventional methods because the conditions under which DNA binds to the silica-based substrate, is washed to remove contaminants, and is eluted from the substrate increase DNA adsorption and dRNP stability relative to conventional silica-based chromatography.

In some embodiments, the method comprises using silica-based chromatography. In general, silica-based chromatography comprises binding nucleic acids to the surface of silica resin or membrane in the presence of a high concentration of chaotropic salts. Contaminants are washed away, and the nucleic acids are eluted from the silica-based resin or membrane in water or a low-salt buffer.

As used herein, a silica or silica-like substrate is a substrate comprising a silicate, such as $SiO_2$. Silica and silica-like materials represent highly adsorptive materials with high surface areas useful for separating different molecules due to differential affinities. Exemplary silica and silica-based materials include, without limitation, silica particles, silica gel particles, resins comprising silica in the form of diatomaceous earth, glass fibers. As used herein, the term "silica-like" refers to surfaces comprising protruding silanol (Si—OH) and siloxane (Si—O—Si) groups. In some embodiments, the silica or silica-like substrate is used as a stationary phase in a chromatographic process. In some embodiments, the silica or silica-like substrate is used as an adsorption agent to isolate or purify a biomolecule comprising a nucleic acid. In some embodiments, the silica substrate is a silica gel or resin comprising amorphous silicic acid polymer, such as, SiO2-nH2O microspheres, having a particle size of about 2 microns or less and/or a pore diameter from about 5 to 150 nanometers.

In some embodiments, the detectable labeled ribonucleoprotein-target nucleic acid complexes are contacted to the silica or silica-like substrate in the presence of a solution comprising one or more of about 0.1 to 1 M L-arginine and 0.1 to 1 M L-lysine. In some embodiments, the solution comprises water, NaCl, ammonium acetate, and one or more of L-arginine, L-lysine, ethanol, and isopropyl alcohol. In some further embodiments, the solution optionally comprises ethanol or isopropyl alcohol. In some further embodiments, the solution also comprises a mild detergent, such as, e.g., 0.01 to 0.1% Tween-20. In some embodiments, such a solution comprises about 1 to about 5.5 M NaCl, 10 mM ammonium acetate (at a pH of about 5.5), and one or more of the following: 0.1-1 M L-arginine, 0.1-1 M L-lysine, and between 0.01 and 0.1% Tween-20 surfactant. In some embodiments, the solution comprises 1 M NaCl, 10 mM ammonium acetate (pH 5.5), and one or more of the following: 1 M L-arginine, 1 M L-lysine, and 0.1% Tween-20. In some embodiments, the solution comprises water, about 1.5 to about 3 M sodium chloride (NaCl), about 10 mM ammonium acetate (having a pH of about 5.5), and one or more of the following: about 0.1 to about 1 M L-arginine, about 0.1 to about 1 M L-lysine, about 15 to about 30% ethanol, and about 5 to about 30% isopropyl alcohol. In some embodiments, the solution comprises about 20-25% ethanol.

As used herein, a detergent is an amphipathic molecule which alters hydrophobic-hydrophilic interactions between biological molecules. A detergent may be anionic, cationic, non-ionic, or zwitterionic. Typically, a detergent comprises a hydrophobic carbon chain and a hydrophilic functional group, such as, a charged functional group. Non-limiting examples of detergents include Tween, Triton X-100, NP-40, polysorbates (e.g. polysorbate 20 or 80), sodium dodecyl sulfate (SDS), CHAPS, and CHAPSO. As used herein, a mild detergent is a detergent condition which disrupts protein-lipid and lipid-lipid associations but not disturb protein-protein interactions or denature proteins.

Following contacting of the sample to the substrate, excess materials (e.g., unbound dRNPs, unbound detectable labels, isothermal amplification reagents, RT reagents, sample debris, and/or excess Qdots) are washed from the silica substrate in presence of a buffered solution (a wash buffer) comprising water and one or more of L-arginine, L-lysine, and isopropyl alcohol. In some embodiments, the wash buffer comprises NaCl, ammonium acetate, and isopropyl alcohol plus one or more of L-arginine, L-lysine. In some cases, the wash buffer comprises 1 M NaCl, 10 mM ammonium acetate (at a pH of about 5.5), and about 5 to about 30% isopropyl alcohol plus one or more of the following: 1 M L-arginine and 1 M L-lysine. In some embodiments, the wash buffer comprises about 5% to about 15% isopropyl alcohol.

Unlike conventional ethanol-containing wash solutions, the wash solution of this disclosure comprises isopropyl alcohol. Without being bound by any particular mode of action or theory, it is believed that isopropyl alcohol is less likely to denature the electrostatic interactions coupling the dRNP and target DNA species adhered to the silica while washing away contaminants.

DNA-dRNP complexes can be eluted from the silica or silica-like substrate by contacting the washed substrate with a low salt, buffered solution comprising one or more of L-arginine and L-lysine. In some cases, the eluting buffer comprises one or more of about 0.5 to 1 M L-arginine and about 0.5 to 1 M L-lysine. In some embodiments, the elution buffer comprises water and one or more of L-arginine, L-lysine, isopropyl alcohol, and a detergent. In some further embodiments, the elution buffer comprises NaCl, ammonium acetate, and about 0.01% to about 0.1% polysorbate-20.

Without being bound to any particular mode of action or theory, it is believed that the incorporation of the interchangeable amino acids L-arginine and L-lysine into the chromatography buffers not only improves DNA binding in low salt conditions, possibly through enhanced hydrophobic interactions and shielding surface silanols, but also competitively inhibits non-specific hydrophobic interactions between soluble proteins and the silica, silica-based, or silica-like substrate. Accordingly, the method of this disclosure provides for isolation of ribonucleoprotein-target nucleic acid complexes with reduced dissociation of the complexes relative to isolation of labeled ribonucleoprotein-target nucleic acid complexes in the absence of the equilibration buffer, wash buffer, and elution buffer. Although streptavidin itself is positively charged and prone to non-specific electrostatic interactions with the silica or silica-like substrate, conjugated Qdots do not appear to be strongly retained on the silica surface.

In some embodiments, silica-based chromatography is used to separate nucleic acid- and target-bound dRNP-quantum dot complexes in a network or web of linked, fluorescent molecules from unbound dRNPs and unincorporated Qdots.

In some embodiments, the methods are performed using siliconized magnetite and/or paramagnetic beads (e.g. Dyna-beads® MyOne™ SILANE, Thermo Fisher Scientific) to isolate DNA-protein complexes for downstream analysis.

In some embodiments, the methods are performed using disposable silica columns. In other embodiments, the methods are performed using plate-based silica columns and a vacuum manifold, for example to achieve high-throughput isolation of DNA-protein complexes for downstream analysis.

Although silica-based isolation of dRNA-target DNA complexes is exemplified in this disclosure, it will be understood to those skilled in the art that the methods of this disclosure can be performed to isolate other types of DNA-protein complexes. Indeed, the methods can be used to isolate any nucleic acid duplex RNP complex provided that the complex does not dissociate at a pH less than 6 and does not denature or dissociate at NaCl concentration between about 0.5 M and 1 M. If these conditions are not met, it may be advantageous to fix the target-dRNP complex using formalin or a similar fixative, although such treatment may alter fluorescence properties, absorbance properties, and/or other physical properties of the isolated complexes.

In some embodiments, the dRNP-target complex is detected via lateral flow on a nitrocellulose membrane. In some embodiments of the lateral flow assay (LFA) method, the nitrocellulose membrane can comprise a negative control, a test line, and a positive control lines corresponding to printed monolayers of BSA-biotin, BSA-biotin-Streptavidin, and heparin sulfate, respectively. In such a case, heparin sulfate acts as a positive control for the Cas-based lateral flow assay (LFA). In one embodiment of a lateral flow assay format, BSA-streptavidin conjugate is applied to a membrane such as nitrocellulose. In some case, the BSA-streptavidin conjugate is applied to the membrane as lines along the length of the membrane, or a portion thereof dRNP-DNA complexes may be applied to one end of the strip and will pass over the streptavidin line due to lateral flow. dRNP-DNA complexes will be retained at the line due to the biotinylated termini of the dCas nuclease. Fluorescence may be measured. In some cases, fluorescence is measured directly via reflection fluorimetry. In some embodiments, the LFA method may be paper based. The LFA method may use microfluidic paper-based LFAs. The paper may be cellulosic paper. The LFA method may also use a paper-based concentration device.

In some embodiments, Cas enzymes are barcoded by appending a predetermined short sequence of nucleotides (e.g., 5-20 nucleotides) to the 3' end of the tracrRNA or the 5' end of the crRNA. In such cases, LFA strips are printed with multiple, separate lines of BSA-conjugated oligonucleotides complementary to the barcode nucleotide sequences. In this way, multiple barcoded Cas molecules corresponding to different targets (e.g., Nucleocapsid, Spike, and RdRp genes from SARS-2-CoV) can be spatially separated on the membrane. Barcoding allows for identification via sequencing, such as, e.g., using a sequencing chip or after tracrRNA sequence amplification by PCR.

In some embodiments, an interconnected network is not formed because a detectable label comprising a plurality of moieties is not present. Instead, a non-bridging monovalent detectable label is used. For example, a deactivated RNA-guided nuclease may be individually tagged using a detectable label (e.g., a monovalent fluorescent) without the possibility of binding to another deactivated RNA-guided nuclease.

As used herein, a monovalent label means a detectable label, which affords binding to a single cognate partner (e.g. an avidin-biotin pair). For example, a monovalent detectable label may comprise or consist essentially of one or more detectable labels covalently attached to a single streptavidin moiety. Then, for example, each "monovalent" labeled-streptavidin can only bind to one biotin-dRNP-target complex at a time. In some embodiments, a monovalent detectable label comprises or consists essentially of one or more fluorophores covalently attached to a single streptavidin moiety. In some embodiments, the detectable label is incorporated into or binds to only the N-terminus or only the C-terminus of the deactivated RNA-guided nuclease.

Accordingly, in another aspect, provided herein is a method for detecting a target nucleic acid in a sample, where the method comprises (a) incubating the sample with a dRNP ribonucleoprotein comprising a deactivated RNA-guided nuclease and a guide RNA (gRNA) configured to bind to the target nucleic acid, wherein the deactivated RNA-guided nuclease comprises at least one monovalent detectable label; under conditions that promote binding of the dRNP to the target nucleic acid; whereby a labeled dRNP-target nucleic acid complex is formed; (b) contacting the labeled ribonucleoprotein-target nucleic complex to a silica or silica-like substrate; (c) washing the contacted silica or silica-like substrate using a wash buffer comprising sodium chloride (NaCl), ammonium acetate, and one or more of L-arginine, L-lysine, and isopropyl alcohol; and (d) eluting labeled ribonucleoprotein-target nucleic acid complexes from the washed substrate, thereby isolating labeled ribonucleoprotein-target nucleic acid complexes. In some embodiments, the buffer conditions of one or more of the contacting, washing, and eluting steps preserves the stability of the complexes with less dissociation than the same method performed without the buffer conditions of one or more of the contacting, washing, and eluting.

As used herein, the term "equilibrated" with regard to a silica or silica-like substrate refers to contacting the silica or silica-like substrate with an aqueous buffer solution (e.g. an equilibration buffer). Equilibration helps sets conditions that can both prepare the substrate for adsorption of a molecule of interest during a contacting of the substrate with a sample and support stability of the molecule of interest during the contacting and later steps. The skilled worker readily understands that in some cases it is desirable to choose an equilibration buffer which replicates or approximates the aqueous buffer solution of the sample to be contacted with the substrate or vice versa.

In some embodiments, the method comprises adsorbing DNA-dRNP to a silica, silica-based, or silica-like substrate. In some embodiments, the substrate is contacted to or coated with an equilibration buffer comprising water, sodium chloride (NaCl), ammonium acetate, L-arginine or L-lysine, and optionally ethanol or isopropyl alcohol. In some embodiments, the substrate is contacted to or coated with an equilibration buffer comprising water, about 1.5 to about 3 M sodium chloride (NaCl), about 10 mM ammonium acetate (having a pH of about 5.5), and one or more of the following: about 0.1 to about 1 M L-arginine, about 0.1 to about 1 M L-lysine, about 15 to about 30% ethanol, and about 5 to about 30% isopropyl alcohol. In some embodiments, the equilibration buffer comprises about 20-25% ethanol.

Provided herein is a composition comprising one or more nucleic acids, such as a gRNA configured to bind to a target nucleic acid. In some embodiments, the composition comprises a gRNA comprising the nucleic acid of any one of SEQ ID NOs: 56-66 or a nucleic acid having at least 90% or 95% identity thereto. In some embodiments the targeting portion of the gRNA targets a region of human papilloma virus (HPV) which may discriminate for high risk of HPV-related cancers. Such targeting sequences are provided as SEQ ID NO: 62-66. In some embodiments, the composition comprises a set of primers comprising the nucleic acids selected from: (a) SEQ ID NOs: 1-6 or six primers having at least 85%, 87%, 90%, 92%, 95%, 97%, or 98% identity thereto; (b) SEQ ID NOs: 7-11 or five primers having at least 85%, 87%, 90%, 92%, 95%, 97%, or 98% identity thereto; (c) SEQ ID NOs: 12-17 or six primers having at least 85%, 87%, 90%, 92%, 95%, 97%, or 98% identity thereto; (d) SEQ ID NOs: 18-22 or five primers having at least 85%, 87%, 90%, 92%, 95%, 97%, or 98% identity thereto; (e) SEQ ID NOs: 23-28 or six primers having at least 85%, 87%, 90%, 92%, 95%, 97%, or 98% identity thereto; (f) SEQ ID NOs: 29-34 or six primers having at least 85%, 87%, 90%, 92%, 95%, 97%, or 98% identity thereto; (g) SEQ ID NOs: 35-39 or five primers having at least 85%, 87%, 90%, 92%, 95%, 97%, or 98% identity thereto; or (h) SEQ ID NOs: 40-43 or four primers having at least 85%, 87%, 90%, 92%, 95%, 97%, or 98% identity thereto; (i) SEQ ID NOs: 44-49 or six primers having at least 90% or 95% identity thereto; and (j) SEQ ID NOs: 50-54 or five primers having at least 90% or 95% identity thereto.

Provided herein is a composition comprising a LAMP primer set, wherein the respective primer set comprises at least four LAMP primers selected from four or more of any one of SEQ ID NOs: 1-54. In some embodiments, the LAMP primer set comprises at least four primers selected from four or more of SEQ ID NOs: 1-6, SEQ ID NOs: 7-11, SEQ ID NOs: 12-17, SEQ ID NOs: 18-22, SEQ ID NOs: 23-28, SEQ ID NOs: 29-34, SEQ ID NOs: 35-39, SEQ ID NOs: 40-43, SEQ ID NOs: 44-49, or SEQ ID NOs: 50-54. In some embodiments, the viral target nucleic acid is a SARS-CoV-2 Spike sequence and the LAMP primer set comprises at least six primers having respectively the sequence of SEQ ID NOs: 1-6. In some embodiments, the viral target nucleic acid is a SARS-CoV-2 ORF1ab sequence and the LAMP primer set comprises at least five primers having respectively the sequence of SEQ ID NOs: 7-11. In some embodiments, the viral target nucleic acid is a SARS-CoV-2 nucleocapsid N2 sequence and the LAMP primer set comprises at least four primers having respectively the sequence of SEQ ID NOs: 12-17. In some embodiments, the viral target nucleic acid is a SARS-CoV-2 nucleocapsid N2 sequence and the LAMP primer set comprises at least four primers having respectively the sequence of SEQ ID NOs: 44-49. In some embodiments, the target nucleic acid is a positive control of a human 18S rRNA sequence and the LAMP primer set comprises at least five primers having respectively the sequence of SEQ ID NOs: 18-22 or the sequence of SEQ ID NOs: 50-54. In some embodiments, the target nucleic acid is a positive control of a human beta-actin ACTB sequence and the LAMP primer set comprises at least four primers selected from any one of SEQ ID NOs: 23-43. In some embodiments, the LAMP primer set comprises six primers having respectively the sequence of SEQ ID NOs: 23-28. In some embodiments, the LAMP primer set comprises six primers having respectively the sequence SEQ ID NOs: 29-34. In some embodiments, the LAMP primer set comprises at least five primers having respectively the sequence of SEQ ID NOs: 35-39. In some embodiments, the LAMP primer set comprises at least four primers having respectively the sequence of SEQ ID NOs: 40-43.

The skilled worker will appreciate that variations of any of the primers mentioned herein may be used in a method or composition of the disclosure. In some embodiments, the LAMP primer set comprises at least four LAMP primers selected from one or more of polynucleotides having at least 85%, 87%, 90%, 92%, 94%, 95%, 96%, 97%, 98%, 99%, or 100% identity respectively to any one of SEQ ID NOs: 1-54. In some embodiments, the viral target nucleic acid is a SARS-CoV-2 Spike sequence and the LAMP primer set comprises at least four primers selected from four or more polynucleotides each having at least 85%, 87%, 90%, 92%, 95%, or 97% identity respectively to any one of SEQ ID NOs: 1-6. In some embodiments, the viral target nucleic acid is a SARS-CoV-2 ORF1ab sequence and the LAMP primer set comprises at least four primers selected from four or more polynucleotides each having at least 85%, 87%, 90%, 92%, 95%, or 97% identity respectively to any one of SEQ ID NOs: 7-11. In some embodiments, the viral target nucleic acid is a SARS-CoV-2 nucleocapsid N2 sequence and the LAMP primer set comprises at least four primers selected from four or more polynucleotides each having at least 85%, 87%, 90%, 92%, 95%, or 97% identity respectively to any one of SEQ ID NOs: 12-17. In some embodiments, the viral target nucleic acid is a SARS-CoV-2 nucleocapsid sequence and the LAMP primer set comprises at least four primers selected from four or more polynucleotides each having at least 85%, 87%, 90%, 92%, 95%, or 97% identity respectively to any one of SEQ ID NOs: 44-49. In some embodiments, the target nucleic acid is a human 18S rRNA sequence and the LAMP primer set comprises at least four primers selected from four or more polynucleotides each having at least 85%, 87%, 90%, 92%, 95%, or 97% identity to any one of SEQ ID NOs: 18-22. In some embodiments, the target nucleic acid is a human beta-actin ACTB sequence and the LAMP primer set comprises at least four primers selected from four or more polynucleotides each having at least 85%, 87%, 90%, 92%, 95%, or 97% identity to any one of SEQ ID NOs: 23-43. In some embodiments, the LAMP primer set comprises (a) SEQ ID NOs: 1-6 or six primers having at least 85%, 87%, 90%, 92%, 95%, 97%, or 98% identity thereto; (b) SEQ ID NOs: 7-11 or five primers having at least 85%, 87%, 90%, 92%, 95%, 97%, or 98% identity thereto; (c) SEQ ID NOs: 12-17 or six primers having at least 85%, 87%, 90%, 92%, 95%, 97%, or 98% identity thereto; (d) SEQ ID NOs: 18-22 or five primers having at least 85%, 87%, 90%, 92%, 95%, 97%, or 98% identity thereto; (e) SEQ ID NOs: 23-28 or six primers having at least 85%, 87%, 90%, 92%, 95%, 97%, or 98% identity thereto; (f) SEQ ID NOs: 29-34 or six primers having at least 85%, 87%, 90%, 92%, 95%, 97%, or 98% identity thereto; (g) SEQ ID NOs: 35-39 or five primers having at least 85%, 87%, 90%, 92%, 95%, 97%, or 98% identity thereto; (h) SEQ ID NOs: 40-43 or four primers having at least 85%, 87%, 90%, 92%, 95%, 97%, or 98% identity thereto; (i) SEQ ID NOs: 44-49 or six primer having at least 85%, 87%, 90%, 92%, 95%, 97%, or 98% identity thereto; or (j) SEQ ID NOs: 50-54 or five primers having at least 85%, 87%, 90%, 92%, 95%, 97%, or 98% identity thereto.

In another aspect, provided herein is an article of manufacture such as a kit, where the kit comprises a silica or silica-like substrate and an equilibration buffer, a wash buffer, and/or an elution buffer. In some embodiments, the kit further comprises instructions for isolating ribonucleoprotein-target nucleic acid complexes by contacting a sample comprising ribonucleoprotein-target nucleic acid complexes to the silica or silica-like substrate and using the equilibration buffer, wash buffer, and elution buffer to isolate ribonucleoprotein-target nucleic acid complexes from the silica or silica-like substrate with reduced dissociation of the complexes relative to isolation in the absence of the equilibration buffer, wash buffer, and/or elution buffer. The equilibration buffer may comprise water, about 1.5 to 3 M NaCl, about 10 mM ammonium acetate (having a pH of about 5.5), and one or more of the following: about 0.1 to 1 M L-arginine, about 0.1 to 1 M L-lysine, about 15 to 30% ethanol, and about 5 to 30% isopropyl alcohol. In some embodiments, the equilibration buffer may comprise about 20 to 25% ethanol. The wash buffer may comprise water, about 1 M NaCl, about 10 mM ammonium acetate (at a pH of about 5.5), and one or more of the following: about 1 M L-arginine, about 1 M L-lysine, and about 5 to 15% isopropyl alcohol. In some embodiments, the wash buffer may comprise a detergent, such as, e.g., about 0.01 to 0.1% polysorbate-20. Preferably, the elution buffer comprises water, NaCl, ammonium acetate, about 5 to 30% isopropyl alcohol, and one or more of about 0.1 to 1 M L-arginine and about 0.1 to 1 M L-lysine.

In another aspect, provided herein is a kit comprising a device or reagent for detecting fluorophore-labeled dRNP-target complexes.

In another aspect, provided herein is one or more buffer solutions useful for separating DNA-associated proteins from other proteins in solution using a silica or silica-like substrate. The buffer solution may be one or more of an equilibration buffer, a wash buffer, and an elution buffer. In some embodiments, the equilibration buffer comprises water, 2 M NaCl, 10 mM ammonium acetate (pH 5.5), and one or more of the following: 1 M L-arginine, 1 M L-lysine, 24% ethanol, and between 5 and 15% isopropyl alcohol. In some embodiments, the wash buffer comprises about 1 M NaCl, about 10 mM ammonium acetate (pH 5.5), and one or more of the following: 1 M L-arginine, 1 M L-lysine, and between 5 and 15% isopropyl alcohol. In some embodiments, the elution buffer comprises NaCl, ammonium acetate, and one or more of L-arginine, L-lysine, and isopropyl alcohol.

Any appropriate sample can be used according to the methods provided herein. In some cases, the sample is a biological sample obtained from an individual (e.g., a human subject, a non-human mammal). The sample is, in some cases, a diagnostic sample. The biological sample can be saliva, a nasopharyngeal swab, blood, serum, sputum, or another biological material. For example, a diagnostic sample for detecting SARS-CoV-2 or another virus can be a saliva sample, a nasopharyngeal swab sample, a blood sample, or a sputum sample. In some cases, samples have been heated prior to performing the other method steps. For instance, samples can be heated to a temperature of about 65° C., which kills the virus and releases nucleic acids. In other cases, samples have been frozen (e.g., at −80° C.) prior to testing. Other samples appropriate for use according to the methods provided herein can also include, without limitation, food samples, drinking water, environmental samples, and agricultural products. In some cases, samples appropriate for use according to the methods provided herein are "non-biological" in whole or in part. Non-biological samples include, without limitation, plastic and packaging materials, paper, clothing fibers, and metal surfaces. In certain embodiments, the methods provided herein are used in food safety and food biosecurity applications, such as screening food products and materials used in food processing or packaging for the presence of pathogens in biological and/or non-biological samples.

The methods of this disclosure can be performed using a sample obtained from any biological entity. The term "biological entity" as used herein means any independent organism or thing, alive or dead, containing genetic material (e.g., nucleic acid) that is capable of replicating either alone or with the assistance of another organism or cell. Sources for nucleic acid-containing biological entities include, without limitation, an organism or organisms including a cell or cells, bacteria, yeast, fungi, algae, viruses, or a sample thereof. Specifically, an organism of the current disclosure includes bacteria, algae, viruses, fungi, and mammals (e.g., humans, non-human mammals). The methods and compositions described herein can be performed using a variety of biological or clinical samples comprising cells (e.g., a cell within live or fixed tissue) that are in any (or all) stage(s) of the cell cycle. The term "sample" includes all types of cell culture, animal or plant tissue, peripheral blood lymphocytes, buccal smears, touch preparations prepared from uncultured primary tumors, cancer cells, bone marrow, cells obtained from biopsy or cells in bodily fluids (e.g., blood, urine, sputum and the like), cells from amniotic fluid, cells from maternal blood (e.g., fetal cells), cells from testis and ovary, and the like. In some cases, samples are obtained by swabbing, washing, or otherwise collecting biological material from a non-biological object such as a medical device, medical instrument, handrail, doorknob, etc. Samples are prepared for assays of this disclosure using conventional techniques, which typically depend on the source from which a sample or specimen is taken. These examples are not to be construed as limiting the sample types applicable to the methods and/or compositions described herein.

The terms "hybridize" and "hybridization" as used herein refer to the association of two nucleic acids to form a stable duplex. Nucleic acids hybridize due to a variety of well characterized physico-chemical forces, such as hydrogen bonding, solvent exclusion, base stacking and the like. An extensive guide to the hybridization of nucleic acids is found in Tijssen, P., editor. 1993. Laboratory Techniques in Biochemistry and Molecular Biology: Hybridization with Nucleic Acid Probes (Vol. 24, Part II, Elsevier B. V., N.Y.). One of skill in the art will understand that "hybridization" as used herein does not require a precise base-for-base complementarity. That is, a duplex can form, between two nucleic acids that contain mismatched base pairs. The conditions under which nucleic acids that are perfectly complementary or that contain mismatched base pairs will hybridize to form a duplex are well known in the art and are described, for example, in Sambrook, J. and Russell, D., editors. 2001. Molecular Cloning: A Laboratory Manual (3$^{rd}$ ed., Cold Spring Harbor Laboratory Press, NY).

As used herein, the term "complementary" refers to a nucleic acid that forms a stable duplex with its "complement". For example, nucleotide sequences that are complementary to each other have mismatches at less than 20% of the bases, at less than about 10% of the bases, preferably at less than about 5% of the bases, and more preferably have no mismatches.

The terms "nucleic acid" and "nucleic acid molecule," as used herein, refer to a compound comprising a nucleobase and an acidic moiety, e.g., a nucleoside, a nucleotide, or a polymer of nucleotides. Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. Nucleic acids and/or other constructs of the invention may be isolated.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain.

Nucleic acids, proteins, and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

Figure 4:
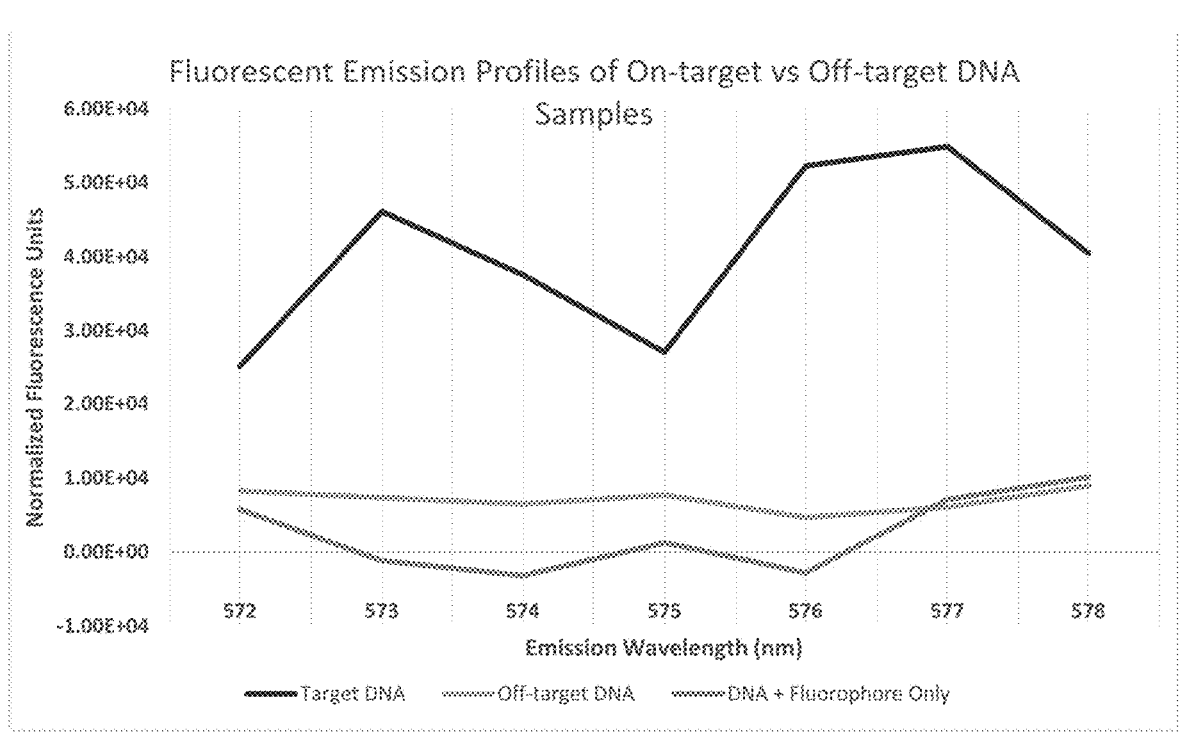
FIG. 4 demonstrates exemplary emission profiles for positive and negative spike-in samples, each containing dRNPs, multivalent fluorescent detectable labels, and an amplified SARS-CoV-2 double-stranded DNA (dsDNA) target nucleic acid or an equivalent amount of non-specific amplified DNA.
Figure 5:
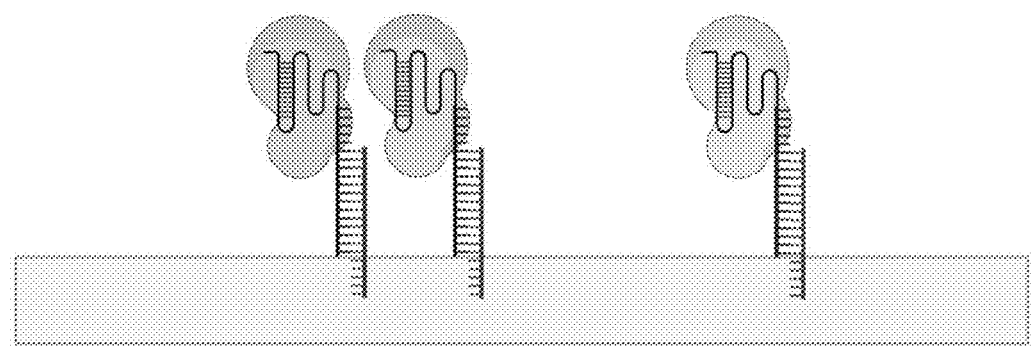
FIG. 5 presents a diagram illustrating spatial separation and multiplexed detection using an embodiment in which barcoded Cas12b-target DNA complexes are provided on a single nitrocellulose strip.

FIG. 4 shows an exemplary assay using spiked in COVID Nucleoprotein (N) dsDNA or an equivalent amount of non-specific DNA. Using the primer set in Table 4, target nucleic acid can be reliably amplified to a yield of approximately 10-15 μg specific product from as little as 1-10 copies of viral RNA in 20-35 minutes, depending on the amount of input material. Additionally, 1-5 copies of viral RNA are reliably detected utilizing the above primers. RT-LAMP reaction products are utilized as the material for direct detection by N gene-specific dRNPs. dRNP and Cas9 buffer solution are added directly to completed LAMP reactions and incubated for downstream analysis. The product can then be detected using SEQ ID NO: 56 as the gRNA. FIG. 5 shows a schematic of multiplex detection of barcoded Cas12b-target DNA complexes on a single nitrocellulose strip.

Figure 6:
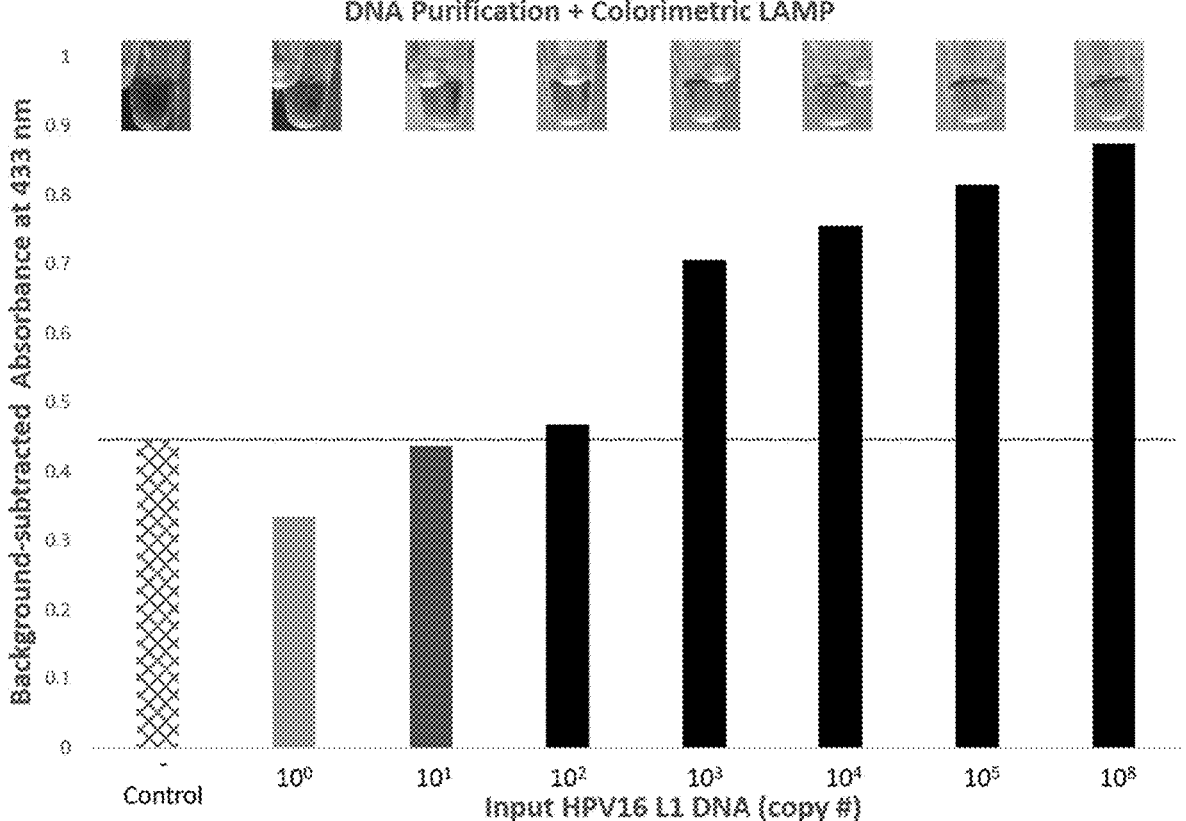
FIG. 6 demonstrates analytic sensitivity of combined magnetic pull-down and RT-LAMP methods.

FIG. 6 shows the sensitivity of the detection of HPV16 using the magnetic pulldown procedure and RT-LAMP reactions described above.

Certain embodiments of the invention are below, numbered 1-32.

1. A method for detecting a target nucleic acid in a sample, the method comprising: (a) contacting the sample with (i) a ribonucleoprotein comprising a deactivated RNA-guided nuclease and a guide RNA (gRNA) configured to bind to the target nucleic acid, wherein the deactivated RNA-guided nuclease comprises a biochemical tag at its N-terminus and C-terminus; and (ii) a detectable label comprising a plurality of moieties capable of binding to the biochemical tag; (b) incubating the contacted sample under conditions that promote binding of the detectable label to the biochemical tag and binding of the ribonucleoprotein to the target nucleic acid, whereby an interconnected network of detectable labeled ribonucleoprotein-target nucleic acid complexes is formed; (c) isolating labeled ribonucleoprotein-target nucleic acid complexes of the interconnected network; and (d) detecting the detectable label or a target nucleic acid of an isolated ribonucleoprotein-target nucleic acid complex.

2. The method of embodiment 1, wherein the biochemical tag comprises biotin and the detectable label comprise a plurality of streptavidin moieties.

3. The method of embodiment 1 or embodiment 2, wherein the isolating comprises contacting the interconnected network of detectable labeled ribonucleoprotein-target nucleic acid complexes to a silica or silica-like substrate.

4. The method of embodiment 3, wherein the isolating comprises silica-based chromatographic separating comprising: (a) contacting the interconnected network of detectable labeled ribonucleoprotein-target nucleic acid complexes to a silica or silica-like substrate in the presence of L-arginine or L-lysine; (b) washing the contacted silica or silica-like substrate using a wash buffer comprising water and one or more of L-arginine, L-lysine, and isopropyl alcohol; and (c) eluting detectable labeled ribonucleoprotein-target nucleic acid complexes from the washed substrate.

5. The method of embodiment 4, wherein the contacting comprises contacting the interconnected network of detectable labeled ribonucleoprotein-target nucleic acid complexes to a silica or silica-like substrate in the presence of a solution comprising water and one or more of L-arginine, L-lysine, isopropyl alcohol, and ethanol; and optionally wherein the solution comprises between 1.5 and 3 M NaCl, 10 mM ammonium acetate (pH 5.5), and one or more of the following: 1 M L-arginine, 1 M L-lysine, between 5% and 15% isopropyl alcohol, and between 15% and 30% ethanol.

6. The method of embodiment 4 or embodiment 5, wherein the wash buffer comprises L-arginine or L-lysine and isopropyl alcohol; and optionally wherein the wash buffer comprises 1 M NaCl, 10 mM ammonium acetate (pH 5.5), and one or more of the following: 1 M L-arginine, 1 M L-lysine, and between 5% and 15% isopropyl alcohol.

7. The method of any one of embodiments 4-6, wherein eluting comprises contacting the washed, contacted substrate to an elution buffer comprising water and one or more of L-arginine, L-lysine, isopropyl alcohol, and a detergent; and optionally wherein the elution buffer comprises NaCl, ammonium acetate, at least 0.5 M L-arginine or at least 0.5 M L-lysine, and between 0.01 and 0.1% polysorbate-20.

8 The method of any one of embodiments 1-7, further comprising prior to step (a), performing isothermal amplification of target nucleic acids in the sample.

9. The method of embodiment 8, wherein isothermal amplification comprises reverse transcription loop-mediated isothermal amplification (RT-LAMP).

10. The method of embodiment 8 or 9, wherein the isothermal amplification comprises a primer set selected from: (a) SEQ ID NOs: 1-6 or six primers having at least 90% or 95% identity thereto; (b) SEQ ID NOs: 7-11 or five primers having at least 90% or 95% identity thereto; (c) SEQ ID NOs: 12-17 or six primers having at least 90% or 95% identity thereto; (d) SEQ ID NOs: 18-22 or five primers having at least 90% or 95% identity thereto; (e) SEQ ID NOs: 23-28 or six primers having at least 90% or 95% identity thereto; (f) SEQ ID NOs: 29-34 or six primers having at least 90% or 95% identity thereto; (g) SEQ ID NOs: 35-39 or five primers having at least 90% or 95% identity thereto; (h) SEQ ID NOs: 40-43 or four primers having at least 90% or 95% identity thereto; (i) SEQ ID NOs: 44-49 or six primers having at least 90% or 95% identity thereto; and (j) SEQ ID NOs: 50-54 or five primers having at least 90% or 95% identity thereto.

11. The method of any one of embodiments 1-10, wherein the gRNA comprises the nucleic acid of any one of SEQ ID NOs: 56-66.

12. The method of any one of embodiments 1-11, wherein the detectable label comprises a fluorophore; and optionally wherein the detectable label is part of a quantum dot.

13. The method of embodiment 12, wherein the detectable label comprises a streptavidin-functionalized fluorophore and the biochemical tag comprises biotin; and optionally wherein the detectable label is part of a quantum dot.

14. The method of any one of embodiments 1-13, wherein the deactivated RNA-guided nuclease is a deactivated Cas9 (dCas9) or deactivated Cas12 (dCas12).

15. The method of any one of embodiments 1-14, wherein the target nucleic acid is a viral nucleic acid.

16. The method of embodiment 15, wherein the viral nucleic acid is from a virus selected from SARS-2-CoV, Influenza A, and Human Papilloma Virus (HPV).

17. The method of any one of embodiments 1-16, wherein the sample is a biological sample selected from: blood, saliva, serum, and sputum.

18. A method for detecting a target nucleic acid in a sample, the method comprising: (a) incubating the sample with a ribonucleoprotein comprising a deactivated RNA-guided nuclease and a guide RNA (gRNA) configured to bind to the target nucleic acid, wherein the deactivated RNA-guided nuclease comprises a detectable label or is bound to a monovalent detectable label, under conditions that promote binding of the ribonucleoprotein to the target nucleic acid; whereby a labeled ribonucleoprotein-target nucleic acid complex is formed; (b) contacting the labeled ribonucleoprotein-target nucleic complex to a silica or silica-like substrate, wherein the silica or silica-like substrate is equilibrated using an equilibration buffer comprising water, sodium chloride (NaCl), ammonium acetate, L-arginine or L-lysine, and optionally ethanol or isopropyl alcohol; (c) washing the contacted silica or silica-like substrate using a wash buffer comprising water, NaCl, ammonium acetate, and isopropyl alcohol, and optionally L-arginine or L-lysine; and (d) eluting the labeled ribonucleoprotein-target nucleic acid complex from the washed substrate.

19. The method of embodiment 18, wherein the equilibration buffer comprises between 1.5 and 3 M NaCl, 10 mM ammonium acetate (pH 5.5), and one or more of the following: 1 M L-arginine, 1 M L-lysine, between 15% and 30% ethanol, and between 5% and 15% isopropyl alcohol.

20. The method of embodiment 18 and embodiment 19, wherein the wash buffer comprises 1 M NaCl, 10 mM ammonium acetate (pH 5.5), and one or more of the following: 1 M L-arginine, 1 M L-lysine, between 5% and 15% isopropyl alcohol, and polysorbate-20.

21. The method of any one of embodiments 18-20, wherein eluting comprises contacting the washed silica or silica-like substrate to an elution buffer comprising water and one or more of L-arginine, L-lysine, isopropyl alcohol, and a detergent; and optionally wherein the elution buffer comprises NaCl, ammonium acetate, and between 0.01% and 0.1% polysorbate-20.

22. The method of any one of embodiments 18-21, further comprising prior to step (a), performing isothermal amplification of target nucleic acids in the sample.

23. The method of embodiment 22, wherein isothermal amplification comprises reverse transcription loop-mediated isothermal amplification (RT-LAMP).

24. The method of embodiment 22 or embodiment 23, wherein the performing isothermal amplification comprises a primer set selected from: (a) SEQ ID NOs: 1-6 or six primers having at least 90% or 95% identity thereto; (b) SEQ ID NOs: 7-11 or five primers having at least 90% or 95% identity thereto; (c) SEQ ID NOs: 12-17 or six primers having at least 90% or 95% identity thereto; (d) SEQ ID NOs: 18-22 or five primers having at least 90% or 95% identity thereto; (e) SEQ ID NOs: 23-28 or six primers having at least 90% or 95% identity thereto; (f) SEQ ID NOs: 29-34 or six primers having at least 90% or 95% identity thereto; (g) SEQ ID NOs: 35-39 or five primers having at least 90% or 95% identity thereto; (h) SEQ ID NOs: 40-43 or four primers having at least 90% or 95% identity thereto; (i) SEQ ID NOs: 44-49 or six primers having at least 90% or 95% identity thereto; and (j) SEQ ID NOs: 50-54 or five primers having at least 90% or 95% identity thereto.

25. The method of any one of embodiments 18-24, wherein the gRNA comprises the nucleic acid of any one of SEQ ID NOs: 56-66.

26. The method of any one of embodiments 18-25, wherein the target nucleic acid is a viral nucleic acid.

27. The method of embodiment 26, wherein the viral nucleic acid is from a virus selected from SARS-2-CoV, Influenza A, and Human Papilloma Virus (HPV).

28. The method of any one of embodiments 18-27, wherein the sample is a biological sample selected from: blood, saliva, serum, and sputum.

29. A composition comprising at least one nucleic acid selected from: a guide RNA comprising the nucleic acid of any one of SEQ ID NOs: 56-66, and a set of primers comprising the nucleic acids selected from: (a) SEQ ID NOs: 1-6 or six primers having at least 90% or 95% identity thereto; (b) SEQ ID NOs: 7-11 or five primers having at least 90% or 95% identity thereto; (c) SEQ ID NOs: 12-17 or six primers having at least 90% or 95% identity thereto; (d) SEQ ID NOs: 18-22 or five primers having at least 90% or 95% identity thereto; (e) SEQ ID NOs: 23-28 or six primers having at least 90% or 95% identity thereto; (f) SEQ ID NOs: 29-34 or six primers having at least 90% or 95% identity thereto; (g) SEQ ID NOs: 35-39 or five primers having at least 90% or 95% identity thereto; (h) SEQ ID NOs: 40-43 or four primers having at least 90% or 95% identity thereto; (i) SEQ ID NOs: 44-49 or six primers having at least 90% or 95% identity thereto; and (j) SEQ ID NOs: 50-54 or five primers having at least 90% or 95% identity thereto.

30. A kit comprising a silica or silica-like substrate, an equilibration buffer, a wash buffer, and an elution buffer; wherein the equilibration buffer comprises water, between 1.5 M and 3 M NaCl, 10 mM ammonium acetate (pH 5.5), and one or more of the following: 1 M L-arginine, 1 M L-lysine, between 15% and 30% ethanol, and between 5% and 15% isopropyl alcohol; wherein the wash buffer comprises water, 1 M NaCl, 10 mM ammonium acetate (pH 5.5), and one or more of the following: 1 M L-arginine, 1 M L-lysine, and between 5% and 15% isopropyl alcohol; and wherein the elution buffer comprises water, NaCl, ammonium acetate, and one or more of L-arginine, L-lysine, isopropyl alcohol, and a detergent.

31. The kit of embodiment 30, further comprising instructions for isolating ribonucleoprotein-target nucleic acid complexes by contacting a sample comprising ribonucleoprotein-target nucleic acid complexes to the silica or silica-like substrate and using the equilibration buffer, wash buffer, and elution buffer to isolate ribonucleoprotein-target nucleic acid complexes from the silica or silica-like substrate with reduced dissociation of the complexes relative to isolation in the absence of the equilibration buffer and wash buffer.

32. The kit of embodiment 30 or embodiment 31, further comprising a composition according to embodiment 29.

In interpreting this disclosure, all terms should be interpreted in the broadest possible manner consistent with the context. It is understood that certain adaptations of the invention described in this disclosure are a matter of routine optimization for those skilled in the art, and can be implemented without departing from the spirit of the invention, or the scope of the appended claims.

So that the compositions and methods provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Embodiments referenced as "comprising" certain elements are also contemplated as "consisting essentially of" and "consisting of" those elements. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The terms "about" and "approximately" shall generally mean an acceptable degree of error for the quantity measured given the nature or precision of the measurements. Typical, exemplary degrees of error are within 10%, and preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated. The term "between" as used herein is inclusive of the endpoints.

Unless otherwise defined, all technical terms used herein have the same meaning as commonly understood by one of ordinary skill in the art to which this invention belongs. As used herein and in the claims, the singular forms "a," "an," and "the" include the singular and the plural reference unless the context clearly indicates otherwise. Thus, for example, a reference to "an agent" includes a single agent and a plurality of such agents. Any reference to "or" herein is intended to encompass "and/or" unless otherwise stated.

Various exemplary embodiments of methods according to this disclosure, in addition to those shown and described herein, will become apparent to those skilled in the art from the foregoing description and the following examples and Exhibit A and fall within the scope of the appended claims. Those skilled in the art will recognize or be able to ascertain using no more than routine experimentation, many equivalents to the specific embodiments of the invention described herein. Such equivalents are intended to be encompassed by the following claims.

We claim:

1. A method for detecting a target nucleic acid in a sample, the method comprising:
  (a) contacting the sample with
    (i) a ribonucleoprotein comprising a deactivated RNA-guided nuclease and a guide RNA (gRNA) configured to bind to the target nucleic acid, wherein the deactivated RNA-guided nuclease comprises a biochemical tag at its N-terminus and C-terminus; and
    (ii) a detectable label comprising a plurality of moieties capable of binding to the biochemical tag;
  (b) incubating the contacted sample under conditions that promote binding of the detectable label to the biochemical tag and binding of the ribonucleoprotein to the target nucleic acid, whereby an interconnected network of detectable labeled ribonucleoprotein-target nucleic acid complexes is formed;

(c) isolating labeled ribonucleoprotein-target nucleic acid complexes of the interconnected network; and (d) detecting the detectable label or a target nucleic acid of an isolated ribonucleoprotein-target nucleic acid complex.

2. The method of claim 1, wherein the biochemical tag comprises biotin and the detectable label comprise a plurality of streptavidin moieties.

3. The method of claim 1, wherein the isolating comprises contacting the interconnected network of detectable labeled ribonucleoprotein-target nucleic acid complexes to a silica or silica-like substrate.

4. The method of claim 3, wherein the isolating comprises silica-based chromatographic separating comprising (a) contacting the interconnected network of detectable labeled ribonucleoprotein-target nucleic acid complexes to a silica or silica-like substrate in the presence of L-arginine or L-lysine;

(b) washing the contacted silica or silica-like substrate using a wash buffer comprising water and one or more of L-arginine, L-lysine, and isopropyl alcohol; and (c) eluting detectable labeled ribonucleoprotein-target nucleic acid complexes from the washed substrate.

5. The method of claim 4, wherein the contacting comprises contacting the interconnected network of detectable labeled ribonucleoprotein-target nucleic acid complexes to a silica or silica-like substrate in the presence of a solution comprising water and one or more of L-arginine, L-lysine, isopropyl alcohol, and ethanol; and optionally wherein the solution comprises between 1.5 and 3 M NaCl, 10 mM ammonium acetate (pH 5.5), and one or more of the following: 1 M L-arginine, 1 M L-lysine, between 5% and 15% isopropyl alcohol, and between 15% and 30% ethanol.

6. The method of claim 4, wherein the wash buffer comprises L-arginine or L-lysine and isopropyl alcohol; and optionally wherein the wash buffer comprises 1 M NaCl, 10 mM ammonium acetate (pH 5.5), and one or more of the following: 1 M L-arginine, 1 M L-lysine, and between 5% and 15% isopropyl alcohol.

7. The method of claim 4, wherein eluting comprises contacting the washed, contacted substrate to an elution buffer comprising water and one or more of L-arginine, L-lysine, isopropyl alcohol, and a detergent; and optionally wherein the elution buffer comprises NaCl, ammonium acetate, at least 0.5 M L-arginine or at least 0.5 M L-lysine, and between 0.01 and 0.1% polysorbate-20.

8. The method of claim 1, further comprising prior to step (a), performing isothermal amplification of target nucleic acids in the sample.

9. The method of claim 8, wherein isothermal amplification comprises reverse transcription loop-mediated isothermal amplification (RT-LAMP).

10. The method of claim 8, wherein performing isothermal amplification comprises using a primer set selected from:

(a) SEQ ID NOs: 1-6 or six primers having at least 90% or 95% identity thereto;

(b) SEQ ID NOs: 7-11 or five primers having at least 90% or 95% identity thereto;

(c) SEQ ID NOs: 12-17 or six primers having at least 90% or 95% identity thereto;

(d) SEQ ID NOs: 18-22 or five primers having at least 90% or 95% identity thereto;

(e) SEQ ID NOs: 23-28 or six primers having at least 90% or 95% identity thereto;

(f) SEQ ID NOs: 29-34 or six primers having at least 90% or 95% identity thereto;

(g) SEQ ID NOs: 35-39 or five primers having at least 90% or 95% identity thereto;

(h) SEQ ID NOs: 40-43 or four primers having at least 90% or 95% identity thereto;

(i) SEQ ID NOs: 44-49 or six primers having at least 90% or 95% identity thereto; and (j) SEQ ID NOs: 50-54 or five primers having at least 90% or 95% identity thereto.

11. The method of claim 1, wherein the gRNA comprises the nucleic acid of any one of SEQ ID NOs: 56-66.

12. The method of claim 1, wherein the detectable label comprises a fluorophore; and optionally wherein the detectable label is part of a quantum dot.

13. The method of claim 12, wherein the detectable label comprises a streptavidin-functionalized fluorophore and the biochemical tag comprises biotin; and optionally wherein the detectable label is part of a quantum dot.

14. The method of claim 1, wherein the deactivated RNA-guided nuclease is a deactivated Cas9 (dCas9) or deactivated Cas12 (dCas12).

15. The method of claim 1, wherein the target nucleic acid is a viral nucleic acid.

16. The method of claim 15, wherein the viral nucleic acid is from a virus selected from SARS-2-CoV, Influenza A, and Human Papilloma Virus (HPV).

17. The method of claim 1, wherein the sample is a biological sample selected from: blood, saliva, serum, and sputum.

* * * * *